(12) United States Patent
Rezania et al.

(10) Patent No.: US 9,752,126 B2
(45) Date of Patent: Sep. 5, 2017

(54) DIFFERENTIATION OF HUMAN PLURIPOTENT STEM CELLS

(71) Applicant: Janssen Biotech, Inc., Horsham, PA (US)

(72) Inventors: Alireza Rezania, Raritan, NJ (US); Benjamin Fryer, Horsham, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 14/963,436

(22) Filed: Dec. 9, 2015

(65) Prior Publication Data

US 2016/0160182 A1 Jun. 9, 2016

Related U.S. Application Data

(62) Division of application No. 12/604,457, filed on Oct. 23, 2009, now Pat. No. 9,234,178.

(60) Provisional application No. 61/110,287, filed on Oct. 31, 2008.

(51) Int. Cl.
*C12N 5/071* (2010.01)

(52) U.S. Cl.
CPC ...... *C12N 5/0676* (2013.01); *C12N 2501/115* (2013.01); *C12N 2501/117* (2013.01); *C12N 2501/155* (2013.01); *C12N 2501/16* (2013.01); *C12N 2501/39* (2013.01); *C12N 2501/405* (2013.01); *C12N 2501/41* (2013.01); *C12N 2501/70* (2013.01); *C12N 2501/998* (2013.01); *C12N 2506/02* (2013.01)

(58) Field of Classification Search
None
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,083,903 A | 7/2000 | Adams et al. |
| 6,087,113 A | 7/2000 | Caplan et al. |
| 6,200,806 B1 | 3/2001 | Thomson |
| 6,261,549 B1 | 7/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 4/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |

(Continued)

FOREIGN PATENT DOCUMENTS

| | | |
|---|---|---|
| CN | 1389565 A | 7/2002 |
| CN | 1602351 A | 3/2005 |
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |

(Continued)

OTHER PUBLICATIONS

Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.
Ackermann, et al., Molecular Regulation of Pancreatic B-Cell Mass Development, Maintenance, and Expansion, Journal of Molecular Endocrinology, 2007, pp. 193-206, vol. 38.

(Continued)

*Primary Examiner* — Catherine S Hibbert
(74) *Attorney, Agent, or Firm* — Lois A. Gianneschi

(57) ABSTRACT

The present invention provides a method for increasing the expression of MAFA in cells expressing markers characteristic of the pancreatic endocrine lineage comprising the steps of culturing the cells expressing markers characteristic of the pancreatic endocrine lineage in medium comprising a sufficient amount of a cyclin-dependent kinase inhibitor to cause an increase in expression of MAFA.

11 Claims, 15 Drawing Sheets

(56) References Cited

U.S. PATENT DOCUMENTS

| | | |
|---|---|---|
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomsom et al. |
| 7,510,876 B2 | 3/2009 | D'Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 2002/0072117 A1 | 6/2002 | Xu |
| 2003/0082155 A1 | 5/2003 | Habener |
| 2003/0138948 A1 | 7/2003 | Fisk et al. |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037488 A1 | 2/2005 | Mitalipova |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0148070 A1 | 7/2005 | Thomson et al. |
| 2005/0158852 A1 | 7/2005 | Wang et al. |
| 2005/0158853 A1 | 7/2005 | D'Amour et al. |
| 2005/0187298 A1 | 8/2005 | Vasudevan et al. |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0154981 A1 | 7/2007 | Hori et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0044390 A1* | 2/2008 | Jin ............ A61K 31/155 424/93.7 |
| 2008/0091234 A1 | 4/2008 | Kladakis et al. |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0053182 A1 | 2/2009 | Ichim et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2011/0151560 A1 | 6/2011 | Xu |
| 2011/0224221 A1* | 9/2011 | Sharpless ............ A61K 31/403 514/252.16 |
| 2011/0229441 A1 | 9/2011 | Benchoua et al. |
| 2011/0281355 A1 | 11/2011 | Xu |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264209 A1 | 10/2012 | Odorico et al. |
| 2013/0189777 A1 | 7/2013 | Rezania |
| 2013/0224156 A1 | 8/2013 | Takahashi et al. |

FOREIGN PATENT DOCUMENTS

| | | |
|---|---|---|
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2479260 B1 | 6/2016 |
| GB | 2484873 B2 | 4/2014 |
| JP | 2005506074 A2 | 3/2003 |
| JP | 2006-500003 A2 | 1/2006 |
| JP | 2008500809 A2 | 1/2008 |
| JP | 2009513143 A2 | 4/2009 |
| KR | 10-2008-0020098 A | 3/2008 |
| RU | 2359671 C2 | 6/2009 |
| WO | WO9219759 A2 | 2/1992 |
| WO | 9847892 A1 | 10/1998 |
| WO | WO9920741 A1 | 4/1999 |
| WO | 0029549 A1 | 5/2000 |
| WO | 0123528 A1 | 4/2001 |
| WO | WO0151616 A2 | 7/2001 |
| WO | WO0181549 A3 | 11/2001 |
| WO | 0246183 A2 | 6/2002 |
| WO | 0246197 A1 | 6/2002 |
| WO | 02086107 A2 | 10/2002 |
| WO | 02092756 A2 | 11/2002 |
| WO | 03026584 A2 | 4/2003 |
| WO | 03029445 A1 | 4/2003 |
| WO | 03033697 A1 | 4/2003 |
| WO | 03042405 A2 | 5/2003 |
| WO | WO0305049 A1 | 6/2003 |
| WO | 03054169 A1 | 7/2003 |
| WO | 03062405 A2 | 7/2003 |
| WO | 03095452 A1 | 11/2003 |
| WO | 03103972 A1 | 12/2003 |
| WO | WO03102134 A2 | 12/2003 |

(56) References Cited

FOREIGN PATENT DOCUMENTS

| | | |
|---|---|---|
| WO | 2004016747 A2 | 2/2004 |
| WO | WO2004011621 A2 | 2/2004 |
| WO | 2004044158 A1 | 5/2004 |
| WO | 2004050827 A2 | 6/2004 |
| WO | 2004055155 A2 | 7/2004 |
| WO | 2004073633 A1 | 9/2004 |
| WO | 2004087885 | 10/2004 |
| WO | WO2004090110 A2 | 10/2004 |
| WO | 2004067001 A1 | 12/2004 |
| WO | 2005080598 A1 | 1/2005 |
| WO | WO2005001077 A2 | 1/2005 |
| WO | 2005017117 A2 | 2/2005 |
| WO | WO2005014799 A1 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | WO2005116073 A3 | 12/2005 |
| WO | 2006020919 A2 | 2/2006 |
| WO | WO2006016999 A1 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006100490 A1 | 9/2006 |
| WO | WO2006094286 A2 | 9/2006 |
| WO | 2006108361 A1 | 10/2006 |
| WO | 2006113470 A2 | 10/2006 |
| WO | 2006114098 A2 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007030870 A1 | 3/2007 |
| WO | WO2007027157 A1 | 3/2007 |
| WO | 2007047509 A1 | 4/2007 |
| WO | 2007051038 A2 | 5/2007 |
| WO | 2007069666 A1 | 6/2007 |
| WO | WO2007082963 A1 | 7/2007 |
| WO | 2007101130 A2 | 9/2007 |
| WO | WO2007103282 A1 | 9/2007 |
| WO | 2007127927 A2 | 11/2007 |
| WO | 2007143193 A1 | 12/2007 |
| WO | 2007149182 A2 | 12/2007 |
| WO | WO2007139929 A2 | 12/2007 |
| WO | 2008004990 A2 | 1/2008 |
| WO | 2008013664 A1 | 1/2008 |
| WO | 2008035110 A1 | 3/2008 |
| WO | 2008036447 A2 | 3/2008 |
| WO | 2008048671 A1 | 4/2008 |
| WO | WO2008048647 A1 | 4/2008 |
| WO | 2009096049 A1 | 5/2008 |
| WO | 2008086005 A1 | 7/2008 |
| WO | 2008094597 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | WO2009048675 A1 | 4/2009 |
| WO | 2009061442 A1 | 5/2009 |
| WO | 2009070592 A1 | 6/2009 |
| WO | 2009096902 A1 | 8/2009 |
| WO | 2009101407 A2 | 8/2009 |
| WO | WO2009105570 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011067465 A1 | 6/2011 |
| WO | 2011108993 A1 | 9/2011 |
| WO | 2011123572 A1 | 10/2011 |
| WO | 2011139628 A1 | 11/2011 |
| WO | 2012019122 A2 | 2/2012 |
| WO | 2012117333 A1 | 9/2012 |
| WO | 2013055834 A2 | 4/2013 |
| WO | 2013184888 A1 | 12/2013 |
| WO | 2014152321 A1 | 9/2014 |

OTHER PUBLICATIONS

Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.

Allegrucci, et al., Differences between Human Embryonic Stem Cell Lines, Human Reproduction Update, Aug. 26, 2006, pp. 1-18, Advance Access.

Amit et al., Human Feeder Layers for Human Embryonic Stem Cells, Biology of Reproduction, Jan. 22, 2003, pp. 2150-2156, vol. 68, No. 6, Society for the Study of Reproduction, Inc.

Amit, et al., Clonally Derived Human Embryonic Stem Cell Lines Maintain Pluripotency and Proliferative Potential for Prolonged Periods of Culture, Developmental Biology, 2000, pp. 271-278, vol. 227.

Amit, et al., Feeder Layer-and Serum-Free Culture of Human Embryonic Stem Cells, Biology of Reproduction, 2004, pp. 837-845, vol. 70.

Arai, et al., Purification of Recombinant Activin A Using the Second Follistatin Domain of Follistatin-Related Gene (FLRG), Protein Expression & Purification, 2006, pp. 78-82, vol. 49.

Armstrong, et al., The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.

Baetge, Production of B-Cells from Human Embryonic Stem Cells, Diabetes, Obesity, Metabolism, 2008, pp. 186-194, vol. 10, Supplement 4.

Balsam, et al., Haematopoeitic Stem Cells Adopt Mature Haeatopoietic Fates in Ischaemic Myocardium, Nature, Apr. 8, 2004, pp. 668-673, vol. 428, Nature Publishing Group.

Barclay, et al., The Leucocyte Antigen Facts Book, the Leucocyte Antigen Facts Book, 1997, Textbook, 2[sup] edition, Academic Press.

Beltrami, et al., Adult Cardiac Stem Cells are Multipotent and Support Myocardial Regeneration, Cell, Sep. 19, 2003, pp. 763-776, vol. 114, Cell Press.

Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.

Blin, et al., A Purified Population of Multipotent Cardiovascular Progenitors Derived from Primate Pluripotent Stem Cells Engrafts in Postmyocardial Infarcted Nonhumans Primates, the Journal of Clinical Investigation, Apr. 2010, pp. 1125-1139, vol. 120, No. 4.

Blyszczuk et al., Expression of Pax4 in embryonic stem cells promotes differentiation of nestin-positive progenitor and insulin-producing cells, Proceedings of the National Academy of Sciences, Feb. 4, 2003, pp. 998-1003, vol. 100-3, National Academy of Sciences.

Bocian-Sobkowska, et al., Polyhormonal Aspect of the Endocrine Cells of the Human Fetal Pancreas, Histochem Cell Biol, 1999, pp. 147-153, vol. 112, Issue 2.

(56) References Cited

OTHER PUBLICATIONS

Bonner-Weir et al., In vitro cultivation of human islets from expanded ductal tissue, Proceedings of the National Academy of Sciences, Jul. 5, 2000, pp. 7999-8004, vol. 97-14, National Academy of Sciences.
Borowiak, et al., How to Make AB Cells, Current Opinion Cell Biology, 2009, pp. 727-732, vol. 21, Issue 6.
Borowitz, et al., Prognostic Significance of Fluorescence Intensity of Surface Marker . . . , Blood, Jun. 1, 1997, pp. 3960-3966, vol. 89-11, American Society of Hematology, Washington, D.C., US.
Braam, et al., Improved Genetic Manipulation of Human Embryonic Stem Cells, Nature Methods, May 2008, pp. 389-392, vol. 5, No. 5.
Brakenhoff et al., Development of a Human Interleukin-6 Receptor Antagonist, Journal of Biological Chemistry, Jan. 7, 1994, pp. 86-93, vol. 269-1, US.
Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.
Brevini, et al., No Shortcuts to Pig Embryonic Stem Cells, Theriogenology, 2010, pp. 544-550, vol. 74.
Brown, et al., Optimal Control of Blood Glucose: The Diabetic Patient or the Machine?, Science Translation Medicine, Apr. 14, 2010, pp. 1-5, vol. 2 Issue 27.
Burkard et al, Conditional Neuronal Nitric Oxide Synthase Overexpression Impairs Myocardial Contractility, Circulation Reseach, Jan. 18, 2007, pp. e32-e44, vol. 100.
Buzzard et al., Karyotype of human ES cells during extended culture, Nature Biotechnology, Apr. 1, 2004, pp. 381-382, vol. 22-4, Nature Publishing Group.
Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.
Castaing, et al., Blood Glucose Normalization Upon Transplantation of Human Embryonic Pancreas into Beta-Cell-Deficient SCID Mice, Diabetologica, 2001, pp. 2066-2076, vol. 44.
Chambers, et al., Functional Expression Cloning of Nanog, a Pluripotency Sustaining Factor in Embryonic Stem Cells, Cell, May 30, 2003, pp. 643-655, vol. 113.
Chapple, et al., Unfolding Retinal Dystrophies: A Role for Molecular Chaperones?, Trends in Molecluar Medicine, 2001, pp. 414-421, vol. 7, No. 9.
Chen, et al., A Small Molecule that Directs Differentiation of Human ESCs into the Pancreatic Lineage, Nature Chemical Biology, Apr. 11, 2009, pp. 258-265, vol. 5, No. 4.
Chen, et al., Chemically Defined Conditions for Human iPSC Derivation and Culture, Nature Methods, 2011, pp. 424-429, vol. 8, Issue 5.
Chen, et al., Differentiation of Rat Marrow Mesencymal Stem Cells in Pancreatic Islet Beta-Cells, World Journal of Gastroenterology, Oct. 15, 2004, pp. 3016-3020, vol. 10.
Cheon et al., Secretory Leukocyte Protease Inhibitor (SLPI) Regulate the Embryonic Differentiation During Periimplantation Stage, Biology of Reproduction, 2007, pp. 64, vol. 77, Society for the Study of Reproduction, Inc.
Cheon, et al., Defined Feeder-Free Culture System of Human Embryonic Stem Cells, Biol Reprod, 2005, 105.046870, DOI10/1095.
Chung, et al., Human Embryonic Stem Cell Lines Generated without Embryo Destruction, Cell Stem Cell, 2008, pp. 113-117, vol. 2.
Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.
Crane, et al., An Embryogenic Model to Explain Cytogenetic Inconsistencies Observed in Chorionic Villus Versus Fetal Tissue, Prenatal Diagnosis, 1988, pp. 119-129, vol. 8.
Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.
D'Amour et al., Efficient differentiation of human embryonic stem cells to definitive endoderm, Nature Biotechnology, Oct. 28, 2005, pp. 1534-1541, vol. 23-12.
D'Amour et al., Production of pancreatic hormone—expressing endocrine cells from human embryonic stem cells, Nature Biotechnology, Oct. 19, 2006, pp. 1392-1401, vol. 24-11, Nature Publishing Group, US.
Damy, et al., Increased Neuronal Nitric Oxide Synthase-Derived no Production in the Failing Human Heart, Research Letters, Apr. 24, 2004, pp. 1365-1367, vol. 363.
David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.
De Rosa, 11-color, 13-parameter flow cytometry: Identification of . . . , Nature, Feb. 1, 2001, pp. 245-248, vol. 7-2, Nature Publishing Group, US.
Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.
Deramaudt, et al., The PDX1 Homeodomain Transcription Factor Negatively Regulates the Pancreatic Ductal Cell-specific Keratin 19 Promoter, Journal of Biological Chemistry, 2006, pp. 38385-38395, vol. 281, No. 50.
Donovan, et al., The End of the Beginning for Pluripotent Stem Cells, Nature, Nov. 2001, pp. 92-97, vol. 414.
Dorrell, et al., Editorial, Stem Cell Research, 2008, pp. 155-156, vol. 1.
Doyle, et al., Cell and Tissue Culture: Laboratory Procedures in Biotechnology, Cell and Tiossue Culture: Laboratory Procedures in Biotechnology, 1995, Textbook, Textbook, Wiley.
Draper, et al., Recurrent Gain of Chromosomes 17q and 12 in Cultured Human Embryonic Stem Cells, Nature Biotechnology, 2004, pp. 53-54, vol. 22, No. 1.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dupont-Gillain, et al., Plasma-Oxidized Polystyrene: Wetting Properties and Surface Reconstruction, Langmuir, 2000, pp. 8194-8200, vol. 16.
Edlund, Pancreatic Organogenisis—Pancreatic Mechanisims and Implications for Therapy, Nature, Jul. 1, 2002, pp. 524-532, vol. 3, Nature Publishing Group, US.
Ellerstrom, et al., Derivation of a Xeno-Free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.
Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, the Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthamology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low 02 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.

(56) References Cited

OTHER PUBLICATIONS

Fidler et al., Selective Immunomodulation by the Antineoplastic Agent Mitoxantrone, Journal of Immunology, Jul. 15, 1986, pp. 727-732, vol. 137-2, American Society of Immunologists, US.
Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.
Fok, et al., Shear-Controlled Single-Step Mouse Embryonic Stem Cell Expansion and Embryoid Body-Based Differentiation, Stem Cells, 2005, pp. 1333-1342, vol. 23.
Frandsen et al., Activin B mediated induction of Pdx1 in human embryonic stemcell derived embryoid bodies, Biochemical and Biophysical Research Communications, Aug. 15, 2007, pp. 568-574, vol. 362, Elsevier Inc.
Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.
Fung, et al., The Effect of Medical Therapy and Islet Cell Transplantation on Diabetic Nephropathy: An Interim Report, Transplantation, Jul. 15, 2007, pp. 17-22, vol. 84, No. 1.
Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, pp. 16806-16811, vol. 103-45, National Academy of Sciences, US.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gershengorn et al., Epithelial-to-Mesenchymal Transition Generates Proliferative Human Islet Precursor Cells, Science, Dec. 24, 2004, pp. 2261-2264, vol. 306, US.
Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, pp. 360-380, vol. 269.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.
Guo, et al., Stem Cells to Pancreatic B-Cells: New Sources for Diabetes Cell Therapy, Endocrine Reviews, May 2009, pp. 214-227, vol. 30, No. 3, the Endocrine Society.
Hadley, et al., Extracellular Matrix Regulates Sertoli Cell Differentiation, Testicular Cord Formation, and Germ Cell Development In Vitro, the Journal of Cell Biology, Oct. 1985, pp. 1511-1522, vol. 101, Rockefeller University Press.
Hamann, et al., Phenotypic and Functional Separation of Memory and and Effector Human CD8+ T Cells, Journal of Experimental Medicine, Mar. 11, 1997, pp. 1407-1418, vol. 186-9, Rockefeller University Press, US.
Harb, et al., The Rho-Rock-Myosin Signaling Axis Determines Cell-Cell Integrity of Self-Renewing Pluripotent Stem Cells, Plos One, 2008, Article e3001, vol. 3, Issue 8.
Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.
Hasegawa, et al., A Method for the Selection of Human Embryonic Stem Cell Sublines with High Replating Efficiency After Single-Cell Dissociation, Stem Cells, 2006, pp. 2649-2660, vol. 24.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.
Henderson, et al., Preimplantation Human Embryos and Embryonic Stem Cells Show Comparable Expression of Stage-Specific Embryonic Antigens, Stem Cells, 2002, pp. 329-337, vol. 20.
Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, pp. 33-37, vol. 47, Portland Press Ltd., GB.
Herzenberg, et al., Fluorescence-activated Cell Sorting, Scientific American, 1976, pp. 108-117, vol. 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Ho, et al., Animal Cell Bioreactors, Animal Cell Bioreactors, 1991, pp. 1-512, Hardcover, Butterworth-Heinemann.
Hoehn, et al., Morphological and Biochemical Heterogeneity of Amniotic Fluid Cells in Culture, Methods in Cell Biology, 1982, pp. 11-34, vol. 26, Academic Press, Inc.
Hori, et al., Growth inhibitors promote differentiation of insulin-producing tissue from embryonic stem cells, Proceedings of the National Academy of Sciences, Dec. 10, 2002, pp. 16105-16110, vol. 99-25, National Academy of Sciences.
Hussain, et al., Stem-Cell Therapy for Diabetes Mellitus, Lancet, 2004, pp. 203-205, vol. 364.
Ianus, et al., In Vivo Derivation of Glucose-Competent Pancreatic Endocrine Cells from Bone Marrow Without Evidence of Cell Fusion, the Journal of Clinical Investigation, Mar. 2003, pp. 843-850, vol. 111, No. 6.
Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.
Int' Anker, et al., Amniotic Fluid as a Novel Source of Mesenchymal Stem Cells for Therapeutic Transplantation, Blood, Aug. 15, 2003, pp. 1548-1549, vol. 102, No. 4.
Inzunza, et al., Derivation of Human Embryonic Stem Cell Lines in Serum Replacement Medium Using Postnatal Human Fibroblasts as Feeder Cells, Stem Cells, 2005, pp. 544-549, vol. 23, AlphaMed Press.
Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.
Jafary, et al., Differential effect of activin on mouse embryonic stem cell differentiation in insulin-secreting cells under nestin-positive selection and spontaneous differentiation protocols, Cell Biology International, 2008, pp. 278-286, vol. 32, Elsevier.
Jeon, et al., Endocrine Cell Clustering During Human Pancreas Development, J Histochem Cytochem, 2009, pp. 811-824, vol. 57, Issue 9.
Jiang, et al., Generation of Insulin-Producing Islet-Like Clusters from Human Embryonic Stem Cells, Stem Cells, 2007, pp. 1940-1953, vol. 25, Issue 8.
Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.
Kahan, Pancreatic Precursors and Differentiated Islet Cell Types from Murine Embryonic Stem Cells, Diabetes, Aug. 2003, pp. 2016-2042, vol. 52.
Kelly, et al., Cell-Surface Markers for the Isolation of Pancreatic Cell Types Derived from Human Embryonic Stem Cells, Nature Biotechnology, 2011, pp. 750-756, vol. 29, Issue 8.
Kicic, et al., Differentiation of Marrow Stromal Cells into Photoreceptors in the Rat Eye, the Journal of Neuroscience, Aug. 27, 2003, pp. 7742-7749, vol. 23, Issue 21.
Kingsley, The TGF-B Supeifamily: New Members, New Receptors, and New Genetic Tests of Function in Different Organisms, Genes & Development, 1994, pp. 133-146, vol. 8, Cold Spring Harbor Laboratory Press.

(56) References Cited

OTHER PUBLICATIONS

Kinkel, et al., Cyp26 Enzymes Function in Endoderm to Regulate Pancreatic Field Size, PNAS, May 12, 2009, pp. 1864-7869, vol. 106, No. 19.

Kleinman et al., Basement Membrane Complexes with Biological Activity, Biochemistry, 1986, pp. 312-318, vol. 25, American Chemical Society.

Klimanskaya, et al., Human Embryonic Stem Cells Derived without Feeder Cells, Lancet, May 2005, pp. 1636-1641, vol. 365, No. 9471.

Koblas, et al., Differentiation of CD133-Positive Pancreatic Cells Into Insulin-Producing Islet-Like Cell Clusters, Transplantation Proceedings, 2008, pp. 415-418, vol. 40.

Kohen, et al., Characterization of Matrigel Interfaces During Defined Human Embryonic Stem Cell Culture, Characterization of Matrigel Interfaces During Defined Human Embryonic Stem Cell Culture, Sep. 3, 2010, pp. 6979, vol. 4.

Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.

Koyangi et al., Inhibitio not the Rho/ROCK Pathway Reduces Apoptosis During Transplantatation of Embryonic Stem Cell-Derived Neural Precursors, Journal of Neurosciene Research, Sep. 7, 2007, pp. 270-280, vol. 86, Wiley-Liss, Inc.

Krapcho et al., Synthesis and Antineoplastic Evaluations of 5,8-Bis[(aminoalkyl)amino]-1-azaanthracene-9,10-diones, Journal of Medical Chemistry, 1985, pp. 1124-1126, vol. 28, American Chemical Society.

Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.

Kron, et al., Expression of Human Activin C Protein in Insect Larvae Infected with a Recombinant Baculovirus, Journal of Virological Methods, 1998, pp. 9-14, vol. 72.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Krutzik, et al., Coordinate Analysis of Murine Immune Cell Surface Markers and Intracellular Phosphoproteins by Flow Cytometry, Journal of Immunology, May 30, 2005, pp. 2357-2365, vol. 175, American Association of Immunologists, Inc., US.

Ku et al., Committing Embryonic Stem Cells to Early Endocrine Pancreas In Vitro, Stem Cells, 2004, pp. 1205-1217, vol. 22, AlphaMed Press.

Kubo et al., Development of definitive endoderm from embryonic stem cells in culture, Development, 2004, p. 1651-1662, vol. 131, the Company of Biologists.

Lanza, et al., Characteristics and Characterization of Human Pluripotent Stem Cells, Stem Cell Anthology, 2010, pp. 141, 142, 144 and 146, 1st Edition.

Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.

Lavon et al., The Effect of Overexpression of Pdx1 and Foxa2 on the Differentiation of Human Embryonic Stem Cells into Pancreatic Cells, Stem Cells, 2006, pp. 1923-1930, vol. 24, Alpha Med Press, IL.

Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

Lee et al., Establishment and Maintenance of Human Embryonic Stem Cell Lines on Human Feeder Cells Derived Tom Uterine Endometrium under Serum-Free Condition, Biology of Reproduction, Aug. 18, 2004, pp. 42-49, vol. 72.

Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.

Levenstein et al., Basic Fibroblast Growth Factor Support of Human Embryonic Stem Cell Self-Renewal, Stem Cells, Nov. 10, 2005, pp. 568-574, vol. 24, AlphaMed Press.

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Lilja et al., Cyclin-dependent Kinase 5 Promotes Insulin Exocytosis, Journal of Biological Chemistry, Jul. 6, 2001, pp. 34199-34205, vol. 36-7, JBC Papers in Press.

Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Puripotency, Annu Rev Genomics Hum Genet, 2011, pp. 165-185, vol. 12.

Ludwig, et al., Derivation of Human Embryonic Stem Cells in Defined Conditions, Nature Biotechnology, Feb. 2006, pp. 185-187, vol. 24 No. 2.

Lumelsky, et al., Differentiation of Embryonic Stem Cells to Insulin-Secreting Structures Similar to Pancreatic Islets, Science, 2001, pp. 1389-1394, vol. 292, HighWire Press.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, Journal of Leukocyte Biology, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

Maherali, et al., Directly Reprogrammed Fibroblasts Show Global Epigenetic Remodeling and Widespread Tissue contribution, Cell Stem Cell, Jul. 2007, pp. 55-70, vol. 1, Elsevier, Inc.

Marshall, et al., Early Micro-and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al., Bioreactors for Tissue Mass Culture: Design, Characterization, and Recent Advances, Biomaterials, Jul. 14, 2005, pp. 7481-7503, vol. 26.

Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.

McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.

McLean et al., Activin A Efficiently Specifies Definitive Endoderm from Human Embryonic Stem Cells Only When Phosphatidylinositol 3-Kinase Signaling is Suppressed, Stem Cells, 2007, pp. 29-38, vol. 25, AlphaMed Press.

McLin, et al., Repression of WNT/(szligbeta)-6atenin Signaling in the Anterior Endoderm is Essential for Liver and Pancreas Development, Development, 2007, pp. 2207-2217, vol. 134, Issue 12.

Meijer, et al., Pharmacological Inhibitors of Glycogen Synthase Kinase 3, Trends in Pharmacological Sciences, Sep. 2004, pp. 471-480, vol. 25, No. 9.

(56) References Cited

OTHER PUBLICATIONS

Micallef et al., Retinoic Acid Induces Pdx1-Positive Endoderm in Differentiating Mouse Embryonic Stem Cells, Diabetes, Feb. 2005, pp. 301-305, vol. 54, American Diabetes Association.
Miller, et al., The Pig as a Model for Human Nutrition, Annual Review of Nutrition, 1987, pp. 361-382, vol. 7, Annual Reviews Inc.
Milunsky, et al., Genetic Disorders and the Fetus: Diagnosis Prevention and Treatment, Pediatric and Developmental Pathology, 2011, pp. 84, vol. 14, Society for Pediatric Pathology.
Mitalipova, et al., Preserving the Genetic Integrity of Human Embyonic Stem Cells, Nature Biotechnology, 2005, pp. 19-20, vol. 23, No. 1.
Mitsui, et al., The Homeoprotein Nanog is Required for Maintenance of Pluripotency in Mouse Epiblast and ES Cells, Cell, May 30, 2003, pp. 631-642, vol. 113, Cell Press.
Miyamoto et al., Human Placenta Feeder Layers Support Undifferentiated Growth of Primate Embryonic Stem Cells, Stem Cells, 2004, pp. 433-440, vol. 22, AlphaMed Press.
Miyazaki et al., Regulated Expression of pdx-1 Promotes In Vitro Differentiation of Insulin-Producing Cells From Embryonic Stem Cells, Diabetes, Apr. 2004, pp. 1030-1037, vol. 53, American Diabetes Association.
Moore, et al., The Corneal Epithelial Stem Cell, DNA and Cell Biology, 2002, pp. 443-451, vol. 21, No. 5/6.
Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.
Movassat, et al., Keratinocyte Growth Factor and Beta-Cell Differentiation in Human Fetal Pancreatic Endocrine Precursor Cells, Diabetologia, 2003, pp. 822-829, vol. 46.
Munoz, et al., Conventional Pluripotency Markers are Unspecific for Bovine Embryonic-Derived Cell-Lines, Theriogenology, 2008, pp. 1159-1164, vol. 69.
Nakagawa, et al., Generation of Induced Pluripotent Stem Cells without Myc from Mouse and Human Fibroblasts, Generation of Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, S75-S80, vol. 22, Supplement 1.
Nicholas et al., A Method for Single-Cell Sorting and Expansion of Genetically modified Human Embryonic Stem Cells, Stem Cells and Development, 2007, pp. 109-117, vol. 16, Mary Ann Liebert, Inc.
Nishimura, et al., Expression of MafA in Pancreatic Progenitors is Detrimental for Pancreatic Development, Developmental Biology, 2009, pp. 108-120, vol. 333.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Oh, et al., Human Embryonic Stem Cells: Technological Challenges Towards Therapy, Clinical and Experimental Pharmacology and Physiology, 2006, pp. 489-495, vol. 33.
Okita, et al., Generation of Germline-Competent Induced Pluripotent Stem Cells, Nature, Jul. 19, 2007, pp. 313-317, vol. 448.
Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.

Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Corning CellBIND Surface: An Improved Surface for Enhanced Cell Attachment, Corning Technical Report, 2005, 8 page report.
Paris, et al., Equine Embryos and Embryonic Stem Cells: Defining Reliable Markers of Pluripotency, Theriogeneology, 2010, pp. 516-524, vol. 74.
Peerani, et al., Niche-Mediated Control of Human Embryonic Stem Cell Self-Renewal and Differentiation, the EMBO Journal, 2007, pp. 4744-4755, vol. 26.
Phillips, et al., Attachment and Growth of Human Embryonic Stem Cells on Microcarriers, Journal of Biotechnology, 2008, pp. 24-32, vol. 138.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Prusa, et al., Oct-4-Expressing Cells in Human Amniotic Fluid: a New Source for Stem Cell Research?, Human Reproduction, 2003, pp. 1489-1493, vol. 18, No. 7.
Rajagopal, et al., Insulin Staining of ES Cell Progeny from Insulin Uptake, Science, Jan. 17, 2003, pp. 363, vol. 299.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Reubinoff et al., Embryonic stem cell lines from human blastocysts: somatic differentiation in vitro, Nature Biotech, Apr. 18, 2000, pp. 399-404, vol. 18, Nature America Inc.
Rezania, Production of Functional Glucagon-Secreting-Cells from Human Embryonic Stem Cells, Diabetes, 2011, pp. 239-247, vol. 60, Issue 1.
Richards et al., Comparative Evaluation of Various Human Feeders for Prolonged Undifferentiated Growth of Human Embryonic Stem Cells, Stem Cells, 2003, pp. 546-556, vol. 21, AlphaMed Publlishing.
Ricordi et al., Automated Method for Isolation of Human Pancreatic Islets, Diabetes, Apr. 1988, pp. 413-420, vol. 37, American Diabetes Association.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adultmesenchymal Stem Cells in the CNS, Society for Neuroscience Abstract Viewer and Itineray Planner, 2002, Program 237.18.
Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.

(56) References Cited

OTHER PUBLICATIONS

Savino et al., Generation of Interleukin-6 Receptor Antagonists by Molecular-Modeling Guided Mutagenesis of Residues Important for gp130 Activation, EMBO Journal, 1994, pp. 1357-1367, vol. 13-6, IT.
Schnier, et al., G1 Arrest and Down-Regulation of Cyclin Elcyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Scullica, et al., Diagnosis and Classification of Macular Degenerations: an Approach Based on Retinal Function Testing, Documenta Ophthalmologica, 2001, pp. 237-250, vol. 102.
Seaberg et al., Cfonal identification of multipotent precursors from adult ~ mouse pancreas that generate neural and pancreatic lineages, Nature Biotechnology, Sep. 2004, pp. 1115-1124, vol. 22, No. 9, Nature Publishing Group.
Segev, et al., Differentiation of Human Embryonic Stem Cells into Insulin-Producing Clusters, Stem Cells, Jan. 1, 2004, pp. 265-274.
Shamblott et al., Derivation of pluripotent stem cells from cultured human primordial germ cells, Developmental Biology, Nov. 1998, pp. 13726-13731, vol. 95, National Academy of Sciences.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, the Massachusetts Medical Society.
Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.
Sherwood, et al., Transcriptional Dynamics of Endodermal Organ Formation, Developmental Dynamics, 2009, pp. 29-42, vol. 238, Issue 1.
Shi et al., Inducing Embryonic Stem Cells to Differentiate into Pancreatic β Cells by a Novel Three-Step Approach with Activin A and All-Trans Retinoic Acid, Stem Cells, 2005, pp. 656-662, vol. 23, AlphaMed Press.
Shindler et al., A synthetic nanofibrillar matrix promotes in vivo-like organization and morphogenesis for cells in culture, Biomaterials, Apr. 18, 2005, pp. 5624-5631, vol. 26, Elsevier.
Shiraki et al., TGF-B Signaling Potentiates Differentiation of Embryonic Stem Cells to Pdx-1 Expressing Endodermal Cells, Genes to Cells, 2005, pp. 503-516, vol. 10, Blackwell Publishing Limited.
Shiraki, et al., Guided Differentiation of Embryonic Stem Cells into Pdx1-Expressing Regional-Specific Definitive Endoderm, Stem Cells, 2008, pp. 874-885, vol. 26.
Sidhu et al., Derivation of Three Clones from Human Embryonic Stem Cell Lines by FACS Sorting and Their Characterization, Stem Cells and Development, 2006, pp. 61-69, vol. 15, Mary Ann Liebert, Inc.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, pp. 749-756, vol. 379, Biochemical Society, GB.

Smith et al., Anti-Interleukin-6 Monocolnal Antibody Induces Regression of Human Prostate Cancer Xenografts in Nude Mice, the Prostate, Mar. 2, 2001, pp. 47-53, vol. 48, Wiley-Liss, Inc.
Soria et al., Insulin-Secreting Cells Derived From Embryonic Stem Cells Normalize Glycemia in Streptozotocin-Induced Diabetic Mice, Diabetes, Feb. 2000, pp. 1-6, vol. 49, American Diabetes Association.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoic Acid Signaling is Required for a Critical Early Step in Zebrafish Pancreatic Development, Current Biology, 2002, pp. 1215-1220, vol. 12, Issue 14.
Stojkovic et al., An Autogeneic Feeder Cell System That Efficiently Supports Growth of Undifferentiated Human Embryonic Stem Cells, Stem Cells, 2005, pp. 306-314, vol. 23, AlphaMed Press.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, pp. 1756-1764, vol. 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Thomson et al., Embryonic Stem Cell Lines Derived from Human Blastocysts, Science, Nov. 6, 1998, pp. 1145-1147, vol. 282, HighWire Press.
Thomson et al., Isolation of a primate embryonic stem cell line, Developmental Biology, Aug. 1995, pp. 7844-7848, vol. 92, Proc. Natl. Acad. Sci, US.
Thomson et al., Primate Embryonic Stem Cells, Current Topics in Developmental Biology, 1998, pp. 133-154, vol. 38, Academic Press, US.
Tomita, et al., Bone Marrow-Derived Stem Cells Can Differentiate into Retinal Cells in Injured Rat Retina, Stem Cells, 2002, pp. 279-283, vol. 20.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tulachan et al., TGF-β isoform signaling regulates secondary transition and mesenchymal-induced endocrine development in the embryonic mouse pancreas, Developmental Biology, 2007, pp. 508-521, vol. 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, pp. 28858-28864, vol. 39, JBC Papers in Press.
Uludag, et al., Technology of Mammalian Cell Encapsulation, Advanced Drug Delivery Reviews, 2000, pp. 29-64, vol. 42.

(56) References Cited

OTHER PUBLICATIONS

Ungrin, et al., Reproducible, Ultra High-Throughput Formation of Multicellular Organization from Single Cell Suspension-Derived Human Embryonic Stem Cell Aggregates, Plos One, 2008, e1565, pp. 1-12, vol. 3, Issue 2.
Unknown, MeSH Descriptor Data, National Library of Medicine—Medical Subject Headings, Feb. 26, 1992.
Unknown, Preserve the Stability of Your Stem Cells, Stem Cells, 2006, Internet Citation.
Vacanti, et al., Selective Cell Transplantation Using Bioabsorbable Artificial Polymers as Matrices, Journal of Pediactric Surgery, Jan. 1988, pp. 3-9, vol. 23-1.
Valet, et al., Pretherapeutic Identification of High-Risk Acute Myeloid Leukemia (AML) Patients from . . . , Clinical Cytometry, Feb. 17, 2003, pp. 4-10, vol. 53B, Wiley-Liss, Inc., US.
Valuer, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, pp. 961-967, vol. 4-1, Nature Reviews, US.
Van Der Windt, et al., The Chioce of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, pp. 138-142, vol. 480, Elsevier.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Derivation and Growing Human Embryonic Stem Cells on Feeders Derived from Themselves, Stem Cells, 2005, pp. 1221-1227, vol. 23, AlphaMed Press.
Wang et al., Relationship of Chemical Structures of Anthraquinones with their Effects onthe Suppression of Immune Responses, International Journal of Immunopharmacology, 1987, pp. 733-739, vol. 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, pp. 1104-1108, vol. 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identities Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
Wiles et al., Embryonic Stem Cell Development in a Chemically Defined Medium, Experimental Cell Research, 1999, pp. 241-248, vol. 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, pp. 972-980, vol. 22, AlphaMed Press.
Ku, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Yang et al., Novel cell immobilization method utilizing centrifugal force to achieve high-density hepatocyte culture in porous scaffold, Journal of Biomed Materials Research, Feb. 27, 2001, pp. 379-386, vol. 55, John Wiley & Sons, Inc.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Acitivity, the Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zhang et al., MafA is a Key Regulator of Glucose-Stimulated Insulin Secretion, Molecular and Cellular Biology, Jun. 2005, pp. 4969-4976, vol. 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, a Doctoral Thesis of Chinese PLA Acadamey of Military Medical Sciences, 2003, pp. 1-127.
Zhang_et_al, Highly Efficient Differentiation of Human ES Cells and iPS Cells into Mature Pancreatic Insulin-Producing Cells, Cell Research, 2009, pp. 429-438, vol. 19, Issue 14.
Zhao et al., The Islet B Cell-enriched MafA Activator is a Key Regulator of Insulin Gene Transcription, Journal of Biological Chemistry, Mar. 25, 2005, pp. 11887-11894, vol. 280-12, the Amerian Society for Biochemistry and molecular Biology, Inc.
Zhao, et al., Derivation and Characterization of Hepatic Progenitor Cells from Human Embryonic Stem Cells, PLoS One Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-6518, vol. 46, Supplement S.
Abe, et al., Evidence That PI3K, Rac, Rho, and Rho Kinase Are Involved in Basic Fibroblast Growth Factor-Stimulated Fibroblast-Collagen Matrix Contraction, Journal of Cellular Biochemistry, 2007, pp. 1290-1299, vol. 102.
Adams, et al., Proteasome Inhibition in Cancer: Development of PS-341, Seminars in Oncology, 2001, pp. 613-619, vol. 28, No. 6.
Ali, et al., Exploitation of Protein Kinase C: A Useful Target for Cancer Therapy, Cancer Treatment Reviews, 2009, pp. 1-8, vol. 35.

(56) References Cited

OTHER PUBLICATIONS

Almond, et al., The Proteasome: A Novel Target for Cancer Chemotherapy, Leukemia, 2002, pp. 433-443, vol. 16.
Amit, et al., Dynamic Suspension Culture for Scalable Expansion of Undifferentiated Human Pluripotent Stem Cells, Nature Protocols, Apr. 7, 2011, pp. 572-579, vol. 6, No. 5.
Assady, et al., Insulin Production by Human Embryonic Stem Cells, Diabetes, 2001, pp. 1691-1697, vol. 50.
Baertschiger, et al., Mesenchymal Stem Cells Derived From Human Exocrine Pancreas Express Transcription Factors Implicated in Beta-Cell Development, Pancreas, 2008, pp. 75-84, vol. 37, No. 1.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.
Best, et al., Embryonic Stem Cells to Beta-Cells by Understanding Pancreas Development, Molecular and Cellular Endorinology, 2008, pp. 86-94, vol. 288.
Bo, et al., Research Progress of Pancreatic Islet Development and Pancreatic Stem Cells, Journal of Clinical Surgery, 2009, pp. 208-210, vol. 17, No. 3.
Brambrink, et al., Sequential Expression of Pluripotency Markers During Direct Reprogramming of Mouse Somatic Cells, Cell Stem Cell, 2008, pp. 151-159, vol. 2.
Bross, et al., Approval Summary for Bortezomib for Injection in the Treatment of Multiple Myeloma, Clinical Cancer Research, Jun. 15, 2004, pp. 3954-3964, vol. 10.
Cao, et al., High Glucose is Necssary for Complete Maturation of Pdx1-VP16-Expressing Hepatic Cells into Functional Insulin-Producing Cells, Diabetes, 2004, pp. 3168-3176, vol. 53.
Chen, et al., Differentiation of Embryonic Stem Cells Towards Pancreatic Progenitor Cells and their Transplantation Into Strepozotocin-Induced Diabetic Mice, Cell Biology International, 2008, pp. 456-461, vol. 32.
Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.
Chetty, et al., A Simple Tool to Improve Pluripotent Stem Cell Differentiation, Nature Methods, 2013, pp. 553-558, vol. 10, No. 6.
Choi, et al., In Vitro Trans-Differentiation of Rat Mesenchymal Cells into Insulin-Producing Cells by Rat Pancreatic Extract, Biochemical and Biophysical Research Communications, 2005, pp. 1299-1305, vol. 330.
Cohick, et al., The Insulin-Like Growth Factors, Annual Reviews Physiol, 1993, pp. 131-153, vol. 55, Annual Reviews Inc.
Cresta, et al., Phase I Study of Bortezomib with Weekly Paclitaxel in Patients with Advanced Solid Tumours, European Journal of Cancer, 2008, pp. 1829-1834, vol. 44.
D'Amour et al, Production of Pancreatic Hormone-Expressing Endocrine Cells From Human Embryonic Stems Cells, Nature Biotechnology, 2006, vol. 24, pp. 1392-1401.
De Coppi, et al., Isolation of Amniotic Stem Cell Lines with Potential for Therapy, Nature Biotechnology, 2007, pp. 100-106, vol. 25, No. 1.
Dekker, et al., Adhesion of Endothelial Cells and Adsorption of Serum Proteins on Gas Plasma-Treated Polytetrafluoroethylene, Biomaterials, 1991, pp. 130-138, vol. 12.
Dufour, et al., Development of an Ectopic Site for Islet Transplantation Using Biodegradable Scaffolds, Tissue Engineering, 2005, pp. 1323-1331, vol. 11, No. 9/10.
Eguizabal, et al., Embryonic Stem Cells/Induced Pluriptent Stem Complete Meiosis from Human Induced Pluripotent Stem Cells, Stem Cells, 2011, pp. 1186-1195, vol. 29.
Florio, et al., Activin A Stimulates Insulin Secretion in Cultured Human Pancreatic Islets, J. Endocrinol. Invest., 2000, pp. 231-234, vol. 23.
Foster, et al., Differentiation of Transplanted Microencapsulated Fetal Pancreatic Cells, Experimental Transplantation, Jun. 15, 2007, pp. 1440-1448, vol. 83, No. 11.
Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.
Gellibert, et al., Identification of 1,5-Naphthyridine Derivatives as a Novel Series of Potent and Selective TGF-B Type I Receptor Inhibitor, J. Med. Chem, 2004, 4494-4506, vol. 47, No. 18.
Gibco, Solutions for Life Science Research and Drug Discovery, Catalogue Cell Culture Products, 2004-2005, pp. 1-4E, 281406 26 5 27.
Gittest, Developmental Biology of the Pancreas: A comprehensive Review, Developmental Biology, 2009, pp. 4-35, vol. 326, No. 1.
Gordon Weir, Do stem cells hold the key to creation of a cure for diabetes?, Diabetes Voice, 2008, pp. 29-31, Edition 53, No. 2.
Gregg Duester, Retionoic Acid Synthesis and Signaling During Early Organogenesis, Cell, 2008, pp. 921-931, vol. 134.
Hainsworth, et al., Retinal Capillar Basement Membrane Thickening in a Porcine Model of Diabetes Mellitus, Comp Med, 2002, pp. 523-529, vol. 52.
Harmon, et al., GDF11 Modulates NGN3+ Islet Progenitor Cell Number and Promotes B-Cell Differentiation in Pancreas Development, Development, 2004, pp. 6163-6174, vol. 131.
Hay, et al., Highly Etlicient Differentiation of hESCs to Functional Hepatic Endoderm Requires ActivinA and Wnt3a Signaling, PNAS, 2008, pp. 12301-12306, vol. 105, No. 34.
Hebrok, et al., Notochord repression of endodermal Sonic hedgehog permits pancreas development, Genes & Development, Jun. 1, 1998, pp. 1705-1713, vol. 12, Issue 11, Cold Spring Harbor Laboratory Press.
Heinis, et al., HIF1a and Pancreatic Beta-Cell Development, the FASEB Journal, 2012, pp. 2734-2742, vol. 26.
Heinis, et al., Oxygen Tension Regulates Pancreatic Beta-Cell Differentiation Through Hypoxia-Inducible Factor 1x, Diabetes, 2010, pp. 662-669, vol. 59.
Heit, et al., Embryonic Stem Cells and Islet Replacement in Diabetes Mellitus, Pediatric Diabetes, 2004, pp. 5-15, vol. 5.
Heremans, et al., Recapitulation of Embryonic Neuroendocrine Differentiation in Adult Human Pancreatic Duct Cells Expressing Neurogenin 3, the Journal of Cell Biology, 2002, pp. 303-311, vol. 159.
Herrera, Adult-Insulin-and Glucagon-Producing Cells Differentiate from Two Independent Cell Lineages, Development, 2000, pp. 2317-2322, vol. 127, No. 11.
Hoffman, et al., Characterization and Culture of Human Embryonic Stem Cells, Nature Biotechnology, 2005, pp. 699-708, vol. 23, No. 6.
Hosoya, et al., Induction of Differentiation of Undifferentiated Cells into Pancreatic Beta-Cells in Vertebrates, Int. J. Dev. Biol., 2012, pp. 313-323, vol. 56.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.
Jaenisch, et al., Stem Cells, The Molecular Circuitry of Pluripotency and Nuclear Reprogramming, cell, Feb. 22, 2008, pp. 567-582, vol. 132, Elsevier Inc.
Jiang, et al., In Vitro Derivation of Functional Insulin-Producing Cells from Human Embryonic Stem Cells, Cell Research, 2007, pp. 333-344, vol. 17.
Karvonen, et al., Incidene of Childhood Type 1 Diabetes Worldwide, Diabetes Care, 2000, pp. 1516-1526, vol. 23, No. 10.
Klajnert, et al., Fluorescence studies on PAMAM dendrimers interactions with bovine serum albumin, Bioelectrochemistry, 2002, pp. 33-35, vol. 55.
Konstantinova__et_al__2007, EphA-Ephrin-A-Mediated Beta Cell Communication Regulates Insulin Secretion from Pancreatic Islets, Cell, Apr. 20, 2007, pp. 359-370, vol. 129.

(56) References Cited

OTHER PUBLICATIONS

Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.

Kubota, et al., Growth factors essential for self-renewal and expansion of mouse spermatogonial stem cells, cell Biology, Nov. 23, 2004, pp. 16489-16494, vol. 101, Issue 47.

Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.

Larsen, et al., Use of the Gootingen Minipig as a Model of Diabetes, with Special Focus on Type 1 Diabetes Research, ILAR Journal, 2004, pp. 303-313, vol. 45, No. 3.

Lee, et al., PKC-Inhibitors Sustain Self-Renewal of Mouse Embryonic Stem Cells Under Hypoxia in Vitro, Experimental and Molecular Medicine, Apr. 2010, pp. 294-301, vol. 43, No. 4.

Lee, et al., Protein Kinase A- and C-Induced Insulin Release from Ca2+-Insensitive Pools, Cellular Signalling, 2003, pp. 529-537, vol. 15.

Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.

Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.

Leon-Quinto, et al., In Vitro Directed Differentiation of Mouse Embryonic Stem Cells into Insulin-Producing Cells, Diabetologia, 2004, pp. 1442-1451, vol. 47, No. 8.

Li, et al., Pluripotency Can be Rapidly and Efficiently Induced in Human Amniotic Fluid-Derived Cells, Human Molecular Genetics, 2009, pp. 4340-4349, vol. 18, No. 22.

Ludwig, et al., Defined Culture Media for Human Embryonic Stem Cells, Embryonic Stem Cells, 2007, pp. 1-16, Springer.

MacFarlane, et al., Glucose Stimulates Translocation of the Homeodomain Transcription Factor PDX1 from the Cytoplasm to the Nucleus in Pancreatic B-Cells, the Journal of Biological Chemistry, 1999, pp. 1011-1016, vol. 274, No. 2.

Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.

Mathis, et al., B-Cell Death During Progression to Diabetes, Nature, 2001, pp. 792-798, vol. 414.

Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.

Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.

Moran, et al., Bidirectional-Barbed Sutured Knotless Running Anastomosis v Classic van Velthoven in a Model System, Journal of Endourology, 2007, pp. 1175-1177, vol. 21, No. 10.

Muchamuel, et al., Preclinical Pharmacology and in Vitro Characterization of PR-047, an Oral Inhibitor of the 20s Proteasome, Blood, Nov. 16, 2008, p. 1257, vol. 112, No. 11.

Murtha, et al., Evaluation of a Novel Technique for Wound Closure Using a Barbed Suture, Cosmetic, Aug. 2, 2005, pp. 1769-1780, vol. 117, No. 6.

Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.

Nie, et al., Scalable Passaging of Adherent Human Pluripotent Stem Cells, PLOS One, 2014, pp. 1-9, vol. 9, Issue 1.

Nostro, et al., Generation of Beta Cells from Human Pluripotent Stem Cells: Potential for Regenerative Medicine, Seminars in Cell & Developmental Biology, 2012, pp. 701-710, vol. 23.

Odom, et al., Control of Pancreas and Liver Gene Expression by HNF Transcription Factors, Science, 2004, pp. 1378-1381, vol. 303, No. 5662.

Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.

Ouziel-Yahalom, et al., Expansion and Redifferentiation of Adult Human Pancreatic islet Cells, Biochemical and Biophysical Research Communications, 2006, pp. 291-298, vol. 341.

Park, et al., Effects of Activin A on Pancreatic Ductal Cells in Streptozotocin-Inducted Diabetic Rats, Experimental Transplantation, 2007, pp. 925-930, vol. 83.

Perrier, et al., Derivation of Midbrain Dopamine Neurons from Human Embryonic Stem Cells, PNAS, Aug. 24, 2004, pp. 12543-12548, vol. 101, No. 34.

Phillips, et al., Directed Differentiation of Human Embryonic Stem Cells into the Pancreatic Endocrine Lineage, Stem Cells and Development, 2007, pp. 561-578, vol. 16, No. 4.

Ptasznik, et al., Phosphatidylinositol 3-Kinase is a Negative Regulator of Cellular Differentiation, the Journal of Cell Biology, 1997, pp. 1127-1136, vol. 137, No. 5.

R&D Systems, Embryonic & Induced Pluripotent Stem Cell Transcription Factors, Embryonic & Induced Pluripotent Stem Cell Transcription Factors, 2013, http://www.mdsystems.com/molecule_group.aspx?r=1&g-3041, 2 page web printout.

R&D Systems, Pancreatic Endoderm, Pancreatic Endoderm, Jun. 24, 2013, http://www.rndsystems.com/molecule_group.aspx?g=801&r, 1 page web printout.

Rajala, et al., Testing of Nine Different Xeno-free Culture Media for Human Embryonic Stem Cell Cultures, Human Reproduction, Jan. 24, 2007, pp. 1231-1238, vol. 22, No. 5.

Ramiya, et al., Reversal of Insulin-Dependent Diabetes Using Islets Generated in vitro from Pancreatic Stem Cells, Nature Medicine, 2000, pp. 278-281, vol. 6.

Ratanasavanh, et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, the Journal of Histochemistry and Cytocheinistry, 1986, pp. 527-533, vol. 34, Issue 4.

Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.

Rezania, E al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.

Rezania, et al., Enrichment of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.

Rezania, et al., Maturation of Human Embryonic Stem Cell-Derived Pancreatic Progenitors into Functional Islets Capable of Treating Pre-Existing Diabetes in Mice, Diabetes, 2012, pp. 2016-2029, vol. 61.

Rezania, et al., Reversal of Diabetes with Insulin-Producing Cells Derived in vitro from Human Pluripotent Stem Cells, Nature Biotechnology, 2014, pp. 1121-1133, vol. 32, No. 11.

Richards, et al., Development of Defined Media for the Serum-Free Expansion of Primary Keratinocytes and Human Embryonic Stem Cells, Tissue Engineering, 2008, pp. 221-232, vol. 14, No. 3.

Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.

Ross, et al., Cytochrome P450s in the Regulation of Cellular Retinoic Acid Metabolism, Annu. Rev. Nutr., 2011, pp. 65-87, vol. 31.

(56) References Cited

OTHER PUBLICATIONS

Rowley, et al., Meeting Lot-Size Challenges of Manufacturing Adherent Cells for Therapy, Cell Therapies Manufacturing, 2012, pp. 16-22, vol. 10, No. 3.
Sander, et al., Homeobox Gene Nkk6.1 Lies Downstream of Nkx2.2 in the Major Pathway of Betta-Cell Formation in the Pancreas, Development, 2000, pp. 5533-5540, vol. 127.
Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182, Issue 2.
Schisler, et al., The NIa6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, vol. 102, No. 20.
Schuldiner, et al., Induced Neuronal Differentiation of Human Embryonic Stem Cells, Brain Research, 2001, pp. 201-205, vol. 913.
Schulz, et al., A Scalable System for Production of Functional Pancreatic Progenitors from Human Embryonic Stem Cells, PLOS One, 2012, pp. 1-17, vol. 7, Issue 5.
Serafimidis, et al., Novel Effectors of Directed and Ngn3-Mediated Differentiation of Mouse Embryonic Stem Cells Into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 84-88, vol. 439.
Shim, et al., Directed Differentiation of Human Embryonic Stem Cells Towards a Pancreatic Cell Fate, Diabetologia, 2007, pp. 1228-1238, vol. 50.
Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.
Sneddon, et al., Self-Renewal of Embryonic-Stem-Cell-Derived Progenitors by Organ-Matched Mesenchyme, Nature, Nov. 29, 2012, pp. 765-770, vol. 491.
Soria, et al., From Stem Cells to Beta Cells: New Strategies in Cell Therapy of Diabetes Mellitus, Diabetologia, 2001, pp. 407-415, vol. 44.
Soria, et al., Insulin-Secreting Cells Derived From Embryonic Stem Cells Normalize Glycemia in Streptozotocin-Induced Diabetic Mice, Diabetes, 2000, pp. 157-162, vol. 49, No. 2.
Spence, et al., Translation Embryology: Using Embryonic Principles to Generate Pancreatic Endocrine Cells from Embryonic Stem Cells, Developmental Dynamics, 2007, pp. 3218-3227, vol. 236.
Stacpoole, et al., Efficient Derivation of Neural Precursor Cells, Spinal Motor Neurons and Midbr, Nat Protoc, 2012, pp. 1-26, vol. 6, Issue 8.
Stafford, et al., Retinoids Signal Directly to Zebrafish Endoderm to Specify Insuilin-Expressing B-cells, Development, 2005, pp. 949-956, vol. 133.
Stoffel, et al., Navigating the Pathway from Embryonic Stem Cells to Beta Cells, Seminars in Cell & Developmental Biology, 2004, pp. 327-336, vol. 15.
Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Suzuken, Differentiation of Multifunctional Stem Cells Using Human Feeder Cells, Research Papers of the Suzuken Memorial Foundation, 2007, pp. 193-197, vol. 24, JP.
Swindle, et al., Swine in Biomedical Research: Management and Models, ILAR News, 1994, pp. 1-5, vol. 36, No. 1.
Thermofisher Scientific, B-27 Serum-Free Supplement (50x) Liquid, Technical Resources, 2016, URL:https://www.thermofisher.com/nl/en/home/technical-resources/media-formulation.250.html, retrieved from the internet.
Totonchi, et al., Feeder-and Serum-Free Establishment and Expansion of Human Induced Pluripotent Stem Cells, Int. J. Dev. Biol., 2010, pp. 8770886, vol. 54.
Tsuchida, et al., Activin Isoforms Signal Through Type I Receptor Serine/Threonin Kinase ALK7, Molecular and Cellular Endocrinology, 2004, pp. 59-65, vol. 22.
Verfaillie, et al., Stem Cells: Hype and Reality, Hematology, 2002, pp. 369-391.
Vieira, et al., Modulation of Neuronal Stem Cell Differentiation by Hypoxia and Reactive Oxygen Species, Progress in Neurobiology, 2011, pp. 444-455, vol. 93.
Wachs, et al., High Efficacy of Clonal Growth and Expansion of Adult Neural Stem Cells, Laboratory Investigation, 2003, pp. 949-962, vol. 83, No. 7.
Wang, et al., Three-Dimensional Differentiation of Embryonic Stem Cells into islet-Like Insulin-Producing Clusters, Tissue Engineering: Part A, 2009, pp. 1941-1952, vol. 15, No. 8.
Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.
White, et al., Complex Regulation of cyp26a1 Creates a Robust Retinoic Acid Gradient in the Zebrafish Embryo, PLOS Biology, 2007, pp. 2522-2533, vol. 5, Issue 11.
Wong, et al., Directed Differentiation of Human Pluripotent Stem Cells into Mature Airway Epithelia Expressing Functional CFTR Protein, Nature Biotechnology, 2012, pp. 876-884, vol. 30, No. 9.
Xudong, et al., Research Progress in Inducing Stem Cels to Differentiate toward the B-like Cells of Pancreatic Islet, Chinese Bulletin of Life Sciences, 2007, pp. 526-530, vol. 19, No. 5.
Yang, et al., Evaluation of Humam MSCs Cell Cycle, Viability and Differentiation in Micromass Culture, Biorheology, 2006, p. 489-496, vol. 43 (English Abstract Only).
Zalzman, et al., Differentiation of Human Liver-Derived, Insulin-Producing Cells Toward the B-Cell Phenotype, Diabetes, 2005, pp. 2568-2575, vol. 54.
Zembower, et al., Peptide Boronic Acids Versatile Synthetic Ligands for Affinity Chromatography of Serine Proteinases, International Journal Peptide Protein, 1996, pp. 405-413, vol. 47.
Zuscik, et al., Regulation of Chondrogenesis and Chondrocyte Differentiation by Stress, J Clin Invest, 2008, pp. 429-438, vol. 118, Issue 2.

\* cited by examiner

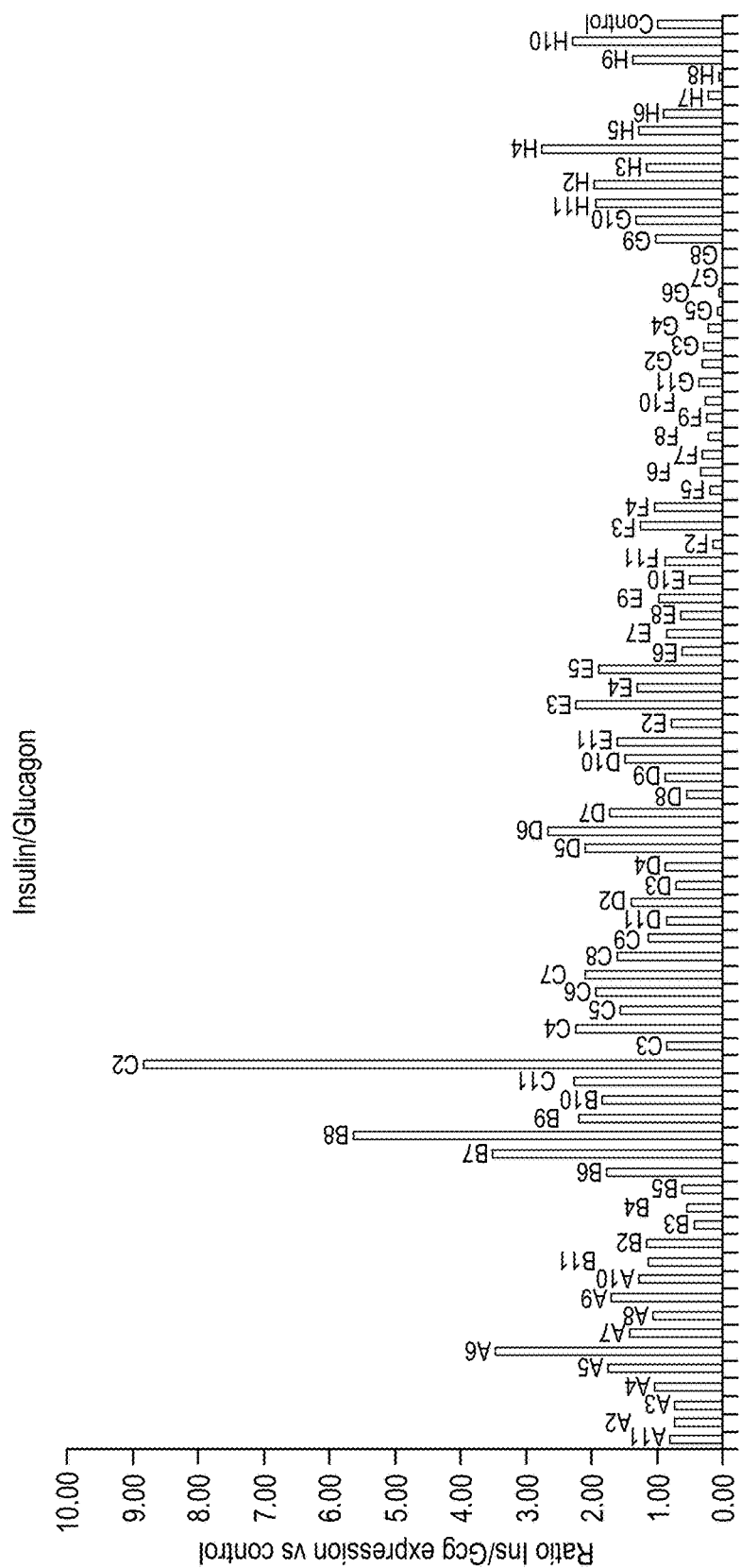

Glucagon

Insulin

MafB

MafA

Somatostatin

Amylase

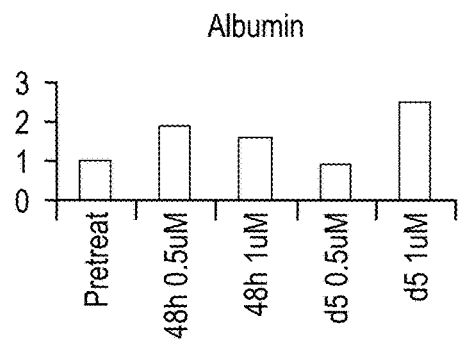
FIG. 3R Albumin
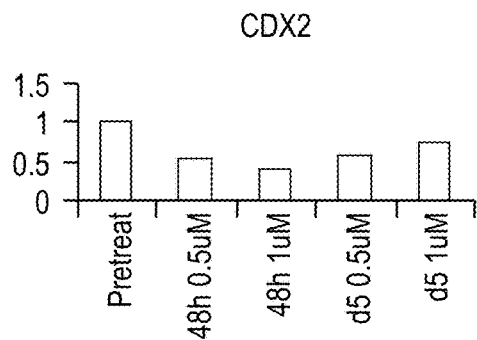
FIG. 3S CDX2
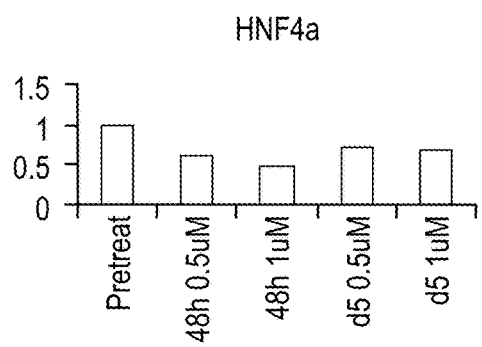
FIG. 3T HNF4a
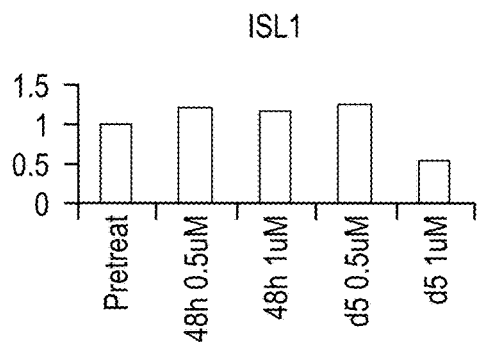
FIG. 3U ISL1
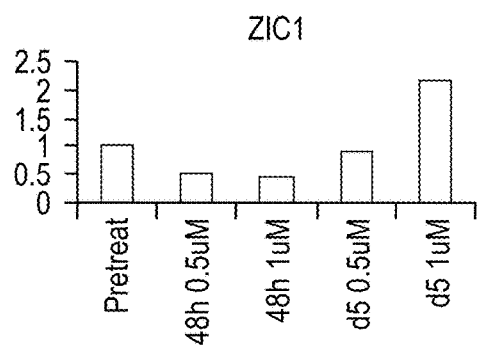
FIG. 3V ZIC1
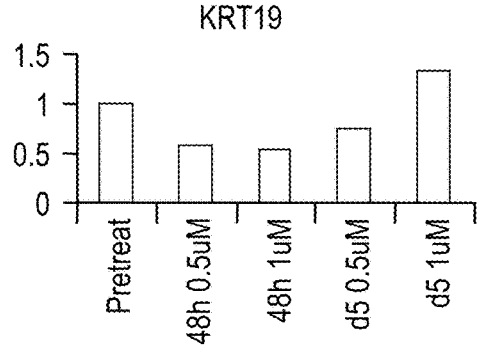
FIG. 3W KRT19

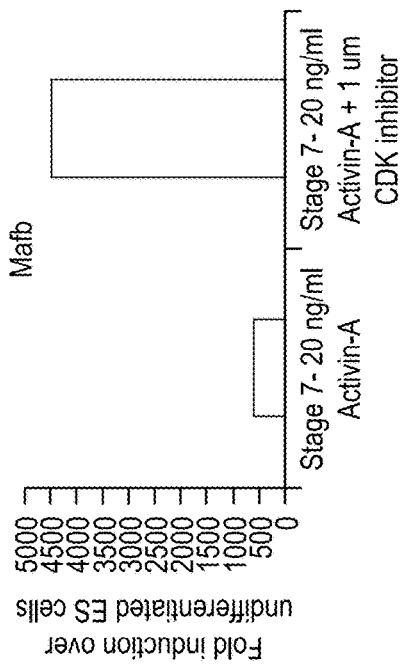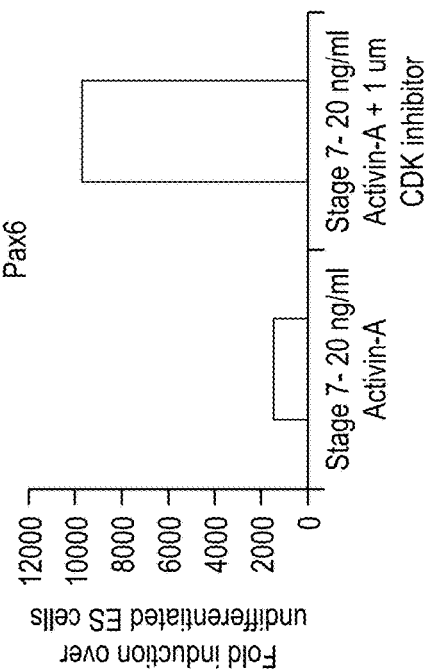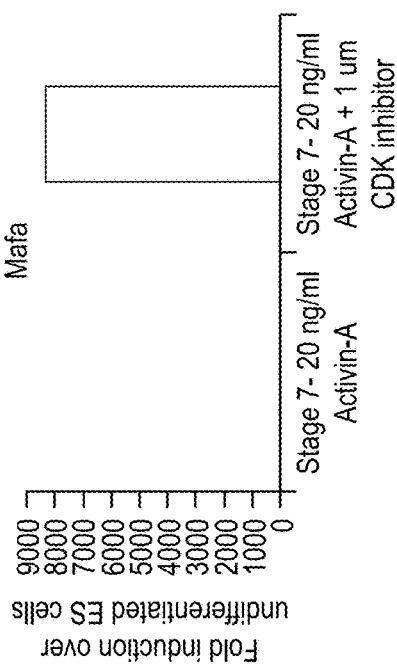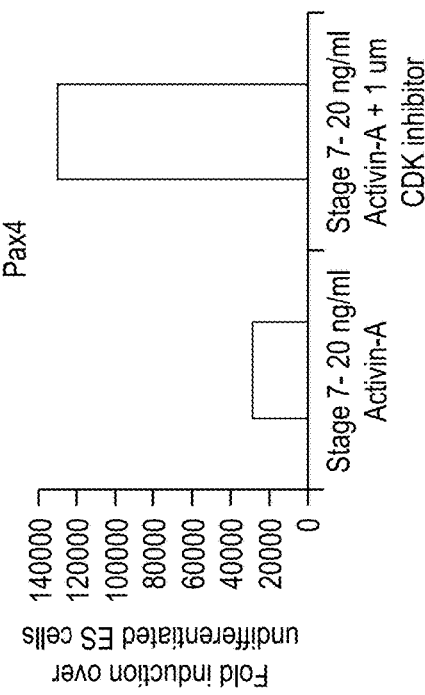

Control

+ CDK inhibitor

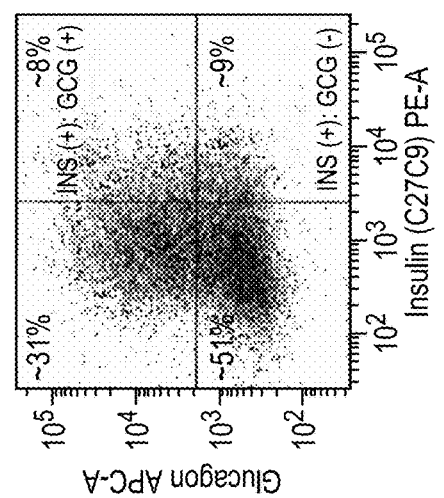
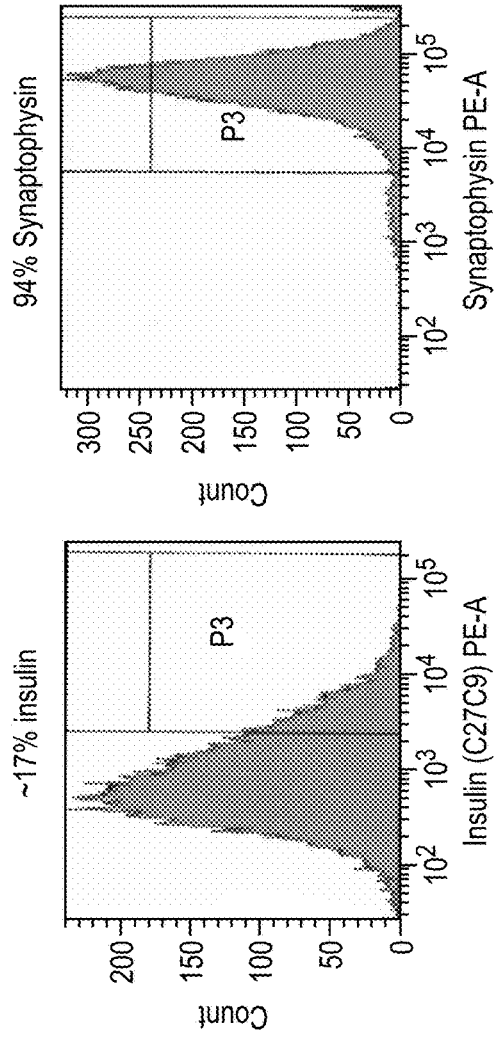
FIG. 7A  FIG. 7B  FIG. 7C

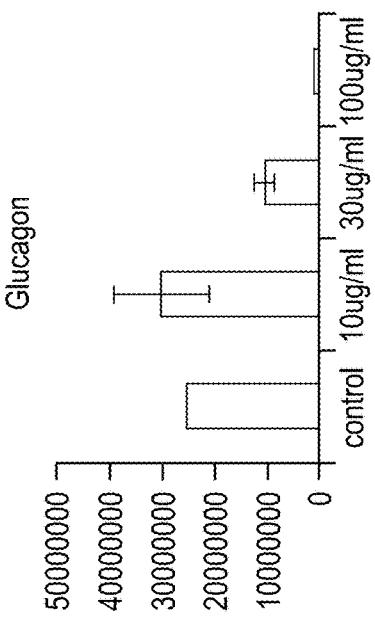
FIG. 10A Insulin
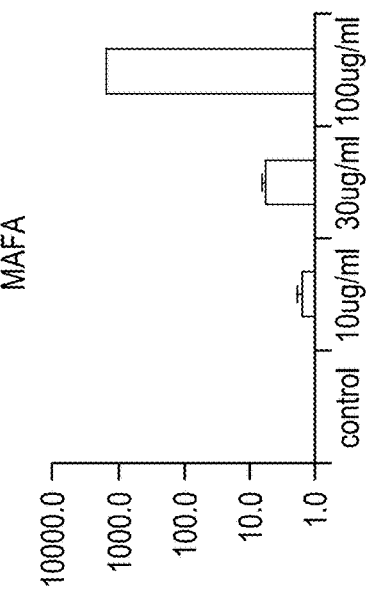
FIG. 10B Glucagon
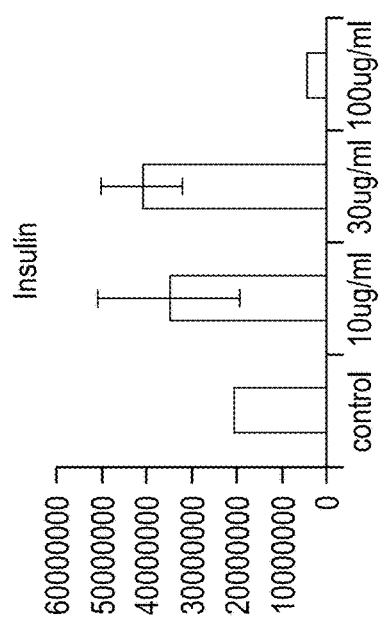
FIG. 10C Somatostatin
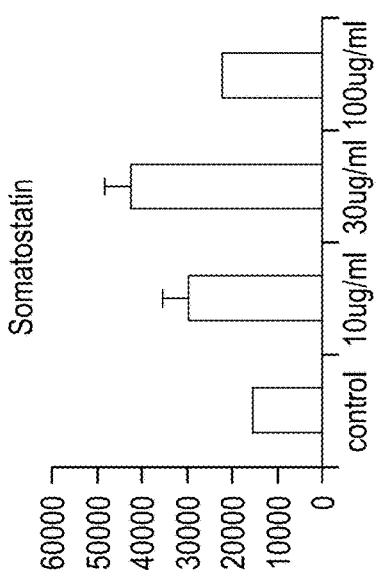
FIG. 10D MAFA

DIFFERENTIATION OF HUMAN PLURIPOTENT STEM CELLS

CROSS-REFERENCE TO RELATED APPLICATIONS

This application is a divisional of U.S. application Ser. No. 12/604,457 filed Oct. 23, 2009 (now U.S. Pat. No. 9,234,178, issued Jan. 12, 2016), which claims priority to provisional Application No. 61/110,287, filed Oct. 31, 2008. The complete disclosures of the aforementioned related patent applications are hereby incorporated herein by reference for all purposes.

FIELD OF THE INVENTION

The present invention provides methods to promote the differentiation of pluripotent stem cells. In particular, the present invention provides a method to increase the expression of MAFA in cells expressing markers characteristic of the pancreatic endocrine lineage.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF-3 beta, GATA4, MIXL1, CXCR4 and SOX17.

Formation of the pancreas arises from the differentiation of definitive endoderm into pancreatic endoderm. Cells of the pancreatic endoderm express the pancreatic-duodenal homeobox gene, PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

In one example, Hori et al. (PNAS 99: 16105, 2002) disclose that treatment of mouse embryonic stem cells with inhibitors of phosphoinositide 3-kinase (LY294002) produced cells that resembled β cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form Pdx1 positive pancreatic endoderm. Retinoic acid is most effective at inducing Pdx1 expression when added to cultures at day 4 of embryonic stem cell differentiation during a period corresponding to the end of gastrulation in the embryo (Diabetes 54:301, 2005).

Miyazaki et al. reports a mouse embryonic stem cell line over-expressing Pdx1. Their results show that exogenous Pdx1 expression clearly enhanced the expression of insulin, somatostatin, glucokinase, neurogenin3, P48, Pax6, and HNF6 genes in the resulting differentiated cells (Diabetes 53: 1030, 2004).

Skoudy et al. reports that activin A (a member of the TGF-β superfamily) upregulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004).

Shiraki et al. studied the effects of growth factors that specifically enhance differentiation of embryonic stem cells into Pdx1 positive cells. They observed that TGF-β2 reproducibly yielded a higher proportion of Pdx1 positive cells (Genes Cells. 2005 June; 10(6): 503-16.).

Gordon et al. demonstrated the induction of brachyury$^+$/HNF-3beta$^+$ endoderm cells from mouse embryonic stem cells in the absence of serum and in the presence of activin along with an inhibitor of Wnt signaling (US 2006/0003446A1).

Gordon et al. (PNAS, Vol 103, page 16806, 2006) states "Wnt and TGF-beta/nodal/activin signaling simultaneously were required for the generation of the anterior primitive streak".

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (Nature Biotechnology 2005). Transplanting these cells under the kidney capsule of mice resulted in differentiation into more mature cells with characteristics of some endodermal organs. Human embryonic stem cell-derived definitive endoderm cells can be further differentiated into Pdx1 positive cells after addition of FGF-10 (US 2005/0266554A1).

D'Amour et al. (Nature Biotechnology—24, 1392-1401 (2006)) states: "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of sodium butyrate and activin A. The cells were then cultured with TGF-β antagonists such as Noggin in combination with EGF or betacellulin to generate Pdx1 positive cells. The terminal differentiation was induced by nicotinamide.

In one example, Benvenistry et al. states: "We conclude that over-expression of Pdx1 enhanced expression of pancreatic enriched genes, induction of insulin expression may require additional signals that are only present in vivo" (Benvenistry et al, Stem Cells 2006; 24:1923-1930).

Cyclins have been implicated in beta cell function. For example, Lilja et al report that Cdk5 is present in the insulin-secreting pancreatic β-cell (J. Biol. Chem., Vol. 276, Issue 36, 34199-34205, Sep. 7, 2001). Lilja et al states "Cdk5 is present in β-cells and acts as a positive regulator of insulin exocytosis."

In another example, Marzo et al states "Cdk4 knockin mice have significantly increased beta cell mass and are physiologically functional, indicating that Cdk4 is a potential target for pancreatic beta cell mass regeneration in Type 1 diabetes" (Diabetalogia, Vol. 47, Number 4, 686-694, Apr. 1, 2004.)

In another example, Ubeda et al report that inhibition of cyclin-dependent kinase 5 activity protects pancreatic beta cells from glucotoxicity (J. Biol. Chem., Vol. 281, Issue 39, 28858-28864, Sep. 29, 2006).

In another example, Wei et al report Cdk5-dependent regulation of glucose-stimulated insulin secretion (Nature Medicine 11, 1104-1108 (1 Oct. 2005.)

In another example, Vanderford et al state "MafA is a basic leucine zipper transcription factor expressed within the beta cells of the pancreas and is required to maintain normal glucose homeostasis as it is involved in various aspects of beta cell biology. MafA protein levels are known to increase in response to high glucose through mechanisms that have yet to be fully characterized. We investigated whether discrete intracellular signaling events control mafA expression. We found that the general kinase inhibitor staurosporine induces mafA expression without altering the stability of the protein. Inhibition of the MAP-kinase JNK mimics the effects of staurosporine on the expression of mafA. Calmodulin kinase and calcium signaling are also important in stimulating mafA expression by high glucose. However, staurosporine, JNK, and calmodulin kinase have different effects on the induction of insulin expression. These data reveal that MafA levels are tightly controlled by the coordinated action of multiple kinase pathways." (Archives of Biochemistry and Biophysics (2008), doi: 10.1016/j.abb.2008.10.001).

Therefore, there still remains a significant need to develop methods for differentiating pluripotent stem cells into pancreatic endocrine cells, pancreatic hormone expressing cells, or pancreatic hormone secreting cells. The present invention provides methods to increase the expression of MAFA in cells expressing markers characteristic of the pancreatic endocrine lineage.

SUMMARY

In one embodiment, the present invention provides a method for increasing the expression of MAFA in cells expressing markers characteristic of the pancreatic endocrine lineage comprising the steps of culturing the cells expressing markers characteristic of the pancreatic endocrine lineage in medium comprising a sufficient amount of a cyclin-dependent kinase inhibitor to cause an increase in expression of MAFA.

BRIEF DESCRIPTION OF THE DRAWINGS

FIG. 1A shows the effect of compounds from the EMD Calbiochem kinase inhibitor library on the ratio of insulin to glucagon expression in cells expressing markers characteristic of the pancreatic endocrine lineage, as determined by real-time PCR. The alphanumeric label corresponds to the compound identity as shown in Table 1.

FIGS. 4A-I show the effect of CDK inhibitor III treatment on the expression of markers characteristic of the pancreatic endocrine lineage in cells treated with Stage 7 of the differentiation protocol described in Example 4.

FIGS. 7A-C show the expression of insulin, synaptophysin and glucagon in insulin-producing cells produced according to the methods described in Example 5. Expression of the proteins indicated was determined by FACS.

FIGS. 10A-D show the effect of genistein on the mRNA expression of insulin, glucagon, somatostatin and MAFA in cells expressing markers characteristic of the pancreatic endocrine lineage, as determined by real-time PCR.

DETAILED DESCRIPTION

Figure 1B:
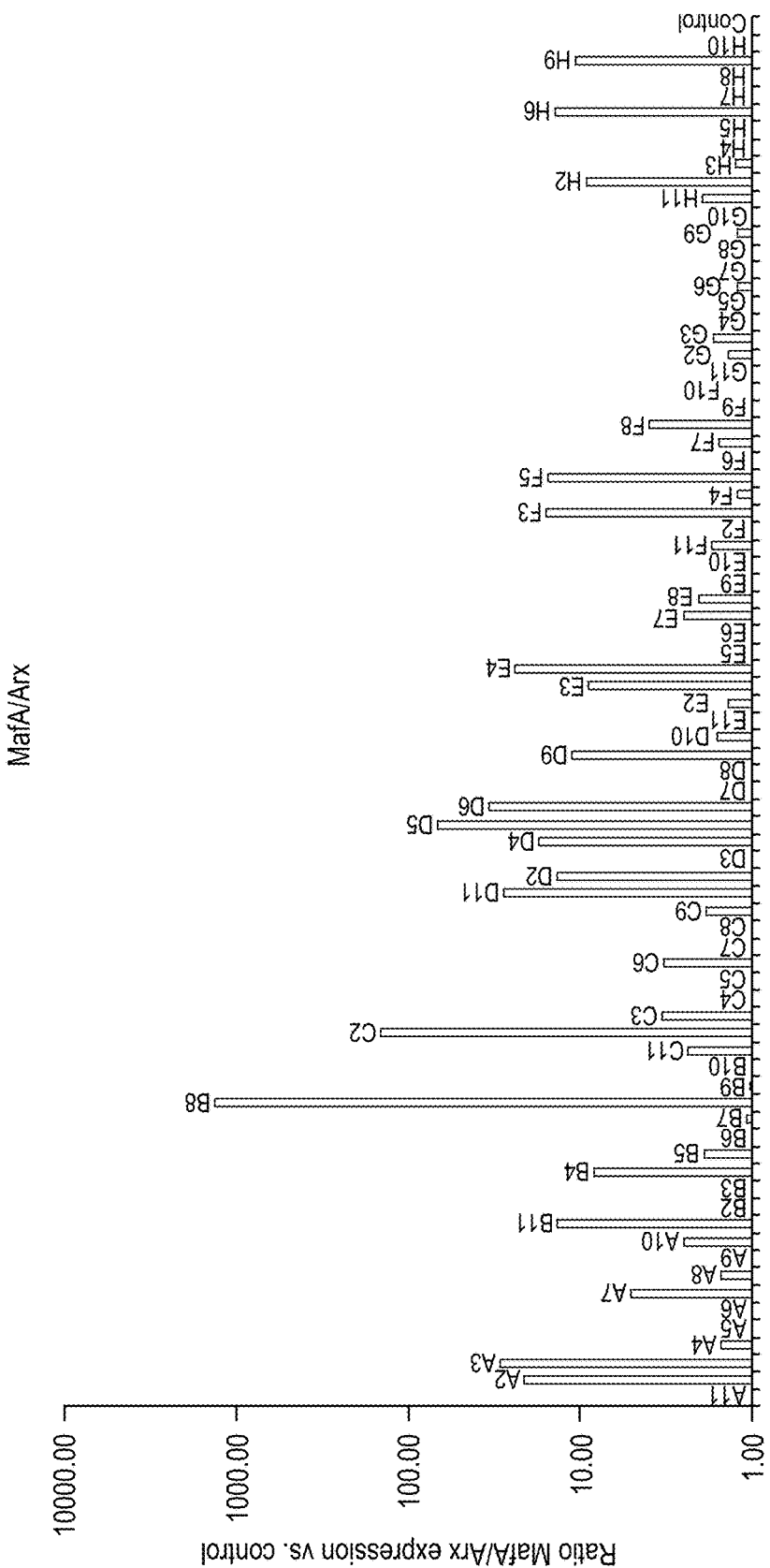
FIG. 1B shows the effect of compounds from the EMD Calbiochem kinase inhibitor library on the ratio of MAFA to ARX4 expression in cells expressing markers characteristic of the pancreatic endocrine lineage, as determined by real-time PCR. The alphanumeric label corresponds to the compound identity as shown in Table 1.

For clarity of disclosure, and not by way of limitation, the detailed description of the invention is divided into the following subsections that describe or illustrate certain features, embodiments or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"β-cell lineage" refers to cells with positive gene expression for the transcription factor PDX-1 and at least one of the following transcription factors: NGN3, NKX2.2, NKX6.1, NEUROD, ISL1, HNF3 beta, MAFA, PAX4, or PAX6. Cells expressing markers characteristic of the β cell lineage include β cells.

"Cells expressing markers characteristic of the definitive endoderm lineage", as used herein, refers to cells expressing at least one of the following markers: SOX17, GATA4, HNF3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage", as used herein, refers to cells expressing at least one of the following markers: PDX1, HNF1 beta, PTF1 alpha, HNF-, or HB9. Cells expressing markers characteristic of the pancreatic endoderm lineage include pancreatic endoderm cells, primitive gut tube cells, and posterior foregut cells.

"Cells expressing markers characteristic of the pancreatic endocrine lineage", as used herein, refers to cells expressing at least one of the following markers: NGN3, NEUROD, ISL1, PDX1, NKX6.1, PAX4, or PTF1 alpha. Cells expressing markers characteristic of the pancreatic endocrine lineage include pancreatic endocrine cells, pancreatic hormone expressing cells, and pancreatic hormone secreting cells, and cells of the β-cell lineage.

"Definitive endoderm", as used herein, refers to cells which bear the characteristics of cells arising from the epiblast during gastrulation and which form the gastrointestinal tract and its derivatives. Definitive endoderm cells express the following markers: HNF3 beta, GATA4, SOX17, Cerberus, OTX2, goosecoid, C-Kit, CD99, or MIXL1.

"Extraembryonic endoderm", as used herein, refers to a population of cells expressing at least one of the following markers: SOX7, AFP, or SPARC.

"Markers", as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell", as used herein, refers to a cell expressing at least one of the following markers: CD48, eomesodermin (EOMES), SOX17, DKK4, HNF3 beta, GSC, FGF17, or GATA6.

"Pancreatic endocrine cell", or "pancreatic hormone expressing cell", as used herein, refers to a cell capable of expressing at least one of the following hormones: insulin, glucagon, somatostatin, or pancreatic polypeptide.

"Pancreatic endoderm cell", as used herein, refers to a cell capable of expressing at least one of the following markers: NGN3, NEUROD, ISL1, PDX1, PAX4, or NKX2.2.

"Pancreatic hormone producing cell", as used herein, refers to a cell capable of producing at least one of the following hormones: insulin, glucagon, somatostatin, or pancreatic polypeptide.

"Pancreatic hormone secreting cell" as used herein, refers to a cell capable of secreting at least one of the following hormones: insulin, glucagon, somatostatin, and pancreatic polypeptide.

"Posterior foregut cell", as used herein, refers to a cell capable of secreting at least one of the following markers: PDX1, HNF1, PTF1 alpha, HNF6, HB9, or PROX1.

"Pre-primitive streak cell", as used herein, refers to a cell expressing at least one of the following markers: Nodal, or FGF8.

"Primitive gut tube cell", as used herein, refers to a cell capable of secreting at least one of the following markers: HNF1, or HNF4A.

"Primitive streak cell", as used herein, refers to a cell expressing at least one of the following markers: Brachyury, Mix-like homeobox protein, or FGF4.

Isolation, Expansion and Culture of Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

For example, Reubinoff et al (Nature Biotechnology 18: 399-404 (2000)) and Thompson et al (Science 6 Nov. 1998: Vol. 282. no. 5391, pp. 1145-1147) disclose the culture of pluripotent stem cell lines from human blastocysts using a mouse embryonic fibroblast feeder cell layer.

Richards et al, (Stem Cells 21: 546-556, 2003) evaluated a panel of 11 different human adult, fetal and neonatal feeder cell layers for their ability to support human pluripotent stem cell culture. Richards et al, states: "human embryonic stem cell lines cultured on adult skin fibroblast feeders retain human embryonic stem cell morphology and remain pluripotent".

US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer.

In another example, Wang et al (Stem Cells 23: 1221-1227, 2005) discloses methods for the long-term growth of human pluripotent stem cells on feeder cell layers derived from human embryonic stem cells.

In another example, Stojkovic et al (Stem Cells 2005 23: 306-314, 2005) disclose a feeder cell system derived from the spontaneous differentiation of human embryonic stem cells.

In a further example, Miyamoto et al (Stem Cells 22: 433-440, 2004) disclose a source of feeder cells obtained from human placenta.

Amit et al (Biol. Reprod 68: 2150-2156, 2003) discloses a feeder cell layer derived from human foreskin.

In another example, Inzunza et al (Stem Cells 23: 544-549, 2005) disclose a feeder cell layer from human postnatal foreskin fibroblasts.

U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure."

In another example, WO2005014799 discloses conditioned medium for the maintenance, proliferation and differentiation of mammalian cells. WO2005014799 states: "The culture medium produced in accordance with the present invention is conditioned by the cell secretion activity of murine cells, in particular, those differentiated and immortalized transgenic hepatocytes, named MMH (Met Murine Hepatocyte)."

In another example, Xu et al (Stem Cells 22: 972-980, 2004) discloses conditioned medium obtained from human embryonic stem cell derivatives that have been genetically modified to over express human telomerase reverse transcriptase.

In another example, US20070010011 discloses a chemically defined culture medium for the maintenance of pluripotent stem cells.

An alternative culture system employs serum-free medium supplemented with growth factors capable of promoting the proliferation of embryonic stem cells. For example, Cheon et al (BioReprod DOI:10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al (Stem Cells 24: 568-574, 2006) disclose methods for the long-term culture of human embryonic stem cells in the absence of fibroblasts or conditioned medium, using media supplemented with bFGF.

In another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, U.S. Pat. No. 6,800,480 states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes non-essential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354 discloses a defined, isotonic culture medium that is essentially feeder-free and serum-free, comprising: a. a basal medium; b. an amount of bFGF sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGF-β) family of proteins, a member of the fibroblast growth factor (FGF) family of proteins, or nicotinamide (NIC) in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, a the suitable culture substrate is MATRIGEL® (Becton Dickenson). MATRIGEL® is a soluble preparation from Engelbreth-Holm Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

Formation of Pancreatic Hormone Producing Cells from Pluripotent Stem Cells

In one embodiment, the present invention provides a method for producing pancreatic hormone producing cells from pluripotent stem cells, comprising the steps of:
  a. Culturing pluripotent stem cells,
  b. Differentiating the pluripotent stem cells into cells expressing markers characteristic of the definitive endoderm lineage, c. Differentiating the cells expressing markers characteristic of the definitive endoderm lineage into cells expressing markers characteristic of the pancreatic endoderm lineage, and d. Differentiating the cells expressing markers characteristic of the pancreatic endoderm lineage into cells expressing markers characteristic of the pancreatic endocrine lineage.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FOXD3, Connexin43, Connexin45, OCT4, SOX2, NANOG, hTERT, UTF1, ZFP42, SSEA3, SSEA4, Tra1-60, or Tra1-81.

Markers characteristic of the definitive endoderm lineage are selected from the group consisting of SOX17, GATA4, HNF3 beta, GSC, CER1, NODAL, FGF8, Brachyury, Mix-like homeobox protein, FGF4 CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of PDX1, HNF1 beta, PTF1 alpha, HNF6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of the pancreatic endocrine lineage are selected from the group consisting of NGN3, NEUROD, ISL1, PDX1, NKX6.1, PAX4, and PTF1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

In one aspect of the present invention, the pancreatic endocrine cell is a cell expressing markers characteristic of the β cell lineage. A cell expressing markers characteristic of the β cell lineage expresses Pdx1 and at least one of the following transcription factors: NGN3, NKX2.2, NKX6.1, NEUROD, ISL1, HNF3 beta, MAFA, PAX4, or PAX6. In one aspect of the present invention, a cell expressing markers characteristic of the β cell lineage is a β cell.

Formation of Cells Expressing Markers Characteristic of the Definitive Endoderm Lineage Pluripotent stem cells may be differentiated into cells expressing markers characteristic of the definitive endoderm lineage by any method in the art or by any method proposed in this invention.

For example, pluripotent stem cells may be differentiated into cells expressing markers characteristic of the definitive endoderm lineage according to the methods disclosed in D'Amour et al, Nature Biotechnology 23, 1534-1541 (2005).

For example, pluripotent stem cells may be differentiated into cells expressing markers characteristic of the definitive endoderm lineage according to the methods disclosed in Shinozaki et al, Development 131, 1651-1662 (2004).

For example, pluripotent stem cells may be differentiated into cells expressing markers characteristic of the definitive endoderm lineage according to the methods disclosed in McLean et al, Stem Cells 25, 29-38 (2007).

For example, pluripotent stem cells may be differentiated into cells expressing markers characteristic of the definitive endoderm lineage according to the methods disclosed in D'Amour et al, Nature Biotechnology 24, 1392-1401 (2006).

For example, pluripotent stem cells may be differentiated into cells expressing markers characteristic of the definitive endoderm lineage by culturing the pluripotent stem cells in medium containing activin A in the absence of serum, then culturing the cells with activin A and serum, and then culturing the cells with activin A and serum of a different concentration. An example of this method is disclosed in Nature Biotechnology 23, 1534-1541 (2005).

For example, pluripotent stem cells may be differentiated into cells expressing markers characteristic of the definitive endoderm lineage by culturing the pluripotent stem cells in medium containing activin A in the absence of serum, then culturing the cells with activin A with serum of another concentration. An example of this method is disclosed in D'Amour et al, Nature Biotechnology, 2005.

For example, pluripotent stem cells may be differentiated into cells expressing markers characteristic of the definitive endoderm lineage by culturing the pluripotent stem cells in medium containing activin A and a Wnt ligand in the absence of serum, then removing the Wnt ligand and culturing the cells with activin A with serum. An example of this method is disclosed in Nature Biotechnology 24, 1392-1401 (2006).

For example, pluripotent stem cells may be differentiated into cells expressing markers characteristic of the definitive endoderm lineage by treating the pluripotent stem cells according to the methods disclosed in U.S. patent application Ser. No. 11/736,908, assigned to LifeScan, Inc.

For example, pluripotent stem cells may be differentiated into cells expressing markers characteristic of the definitive endoderm lineage by treating the pluripotent stem cells according to the methods disclosed in U.S. patent application Ser. No. 11/779,311, assigned to LifeScan, Inc.

For example, pluripotent stem cells may be differentiated into cells expressing markers characteristic of the definitive endoderm lineage by treating the pluripotent stem cells according to the methods disclosed in U.S. patent application Ser. No. 60/990,529.

For example, pluripotent stem cells may be differentiated into cells expressing markers characteristic of the definitive endoderm lineage by treating the pluripotent stem cells according to the methods disclosed in U.S. patent application Ser. No. 61/076,889.

For example, pluripotent stem cells may be differentiated into cells expressing markers characteristic of the definitive endoderm lineage by treating the pluripotent stem cells according to the methods disclosed in U.S. patent application Ser. No. 61/076,900.

For example, pluripotent stem cells may be differentiated into cells expressing markers characteristic of the definitive endoderm lineage by treating the pluripotent stem cells according to the methods disclosed in U.S. patent application Ser. No. 61/076,908.

For example, pluripotent stem cells may be differentiated into cells expressing markers characteristic of the definitive endoderm lineage by treating the pluripotent stem cells according to the methods disclosed in U.S. patent application Ser. No. 61/076,915.

Differentiation of Cells Expressing Markers Characteristic of the Definitive Endoderm Lineage Formation of cells expressing markers characteristic of the definitive endoderm lineage may be determined by testing for the presence of the markers before and after following a particular protocol. Pluripotent stem cells typically do not express such markers. Thus, differentiation of pluripotent cells is detected when cells begin to express them.

The efficiency of differentiation may be determined by exposing a treated cell population to an agent (such as an antibody) that specifically recognizes a protein marker expressed by cells expressing markers characteristic of the definitive endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, Connexin43, Connexin45, OCT4, SOX2, NANOG, hTERT, UTF1, ZFP42, SSEA3, SSEA4, Tra1-60, or Tra1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Formation of Cells Expressing Markers Characteristic of the Pancreatic Endoderm Lineage Cells expressing markers characteristic of the definitive endoderm lineage may be differentiated into cells expressing markers characteristic of the pancreatic endoderm lineage by any method in the art or by any method proposed in this invention.

For example, cells expressing markers characteristic of the definitive endoderm lineage may be differentiated into cells expressing markers characteristic of the pancreatic endoderm lineage according to the methods disclosed in D'Amour et al, Nature Biotechnology 24, 1392-1401 (2006).

For example, cells expressing markers characteristic of the definitive endoderm lineage are further differentiated into cells expressing markers characteristic of the pancreatic endoderm lineage, by treating the cells expressing markers characteristic of the definitive endoderm lineage with a fibroblast growth factor and the hedgehog signaling pathway inhibitor KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in Nature Biotechnology 24, 1392-1401 (2006).

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/736,908, assigned to LifeScan, Inc.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/779,311, assigned to LifeScan, Inc.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage according to the methods disclosed in U.S. patent application Ser. No. 60/990,529.

Detection of Cells Expressing Markers Characteristic of the Pancreatic Endoderm Lineage Markers characteristic of the pancreatic endoderm lineage are well known to those skilled in the art, and additional markers characteristic of the pancreatic endoderm lineage continue to be identified. These markers can be used to confirm that the cells treated in accordance with the present invention have differentiated to acquire the properties characteristic of the pancreatic endoderm lineage. Pancreatic endoderm lineage specific markers include the expression of one or more transcription factors such as, for example, HLXB9, PTF1 alpha, PDX1, HNF6, or HNF1 beta.

The efficiency of differentiation may be determined by exposing a treated cell population to an agent (such as an antibody) that specifically recognizes a protein marker expressed by cells expressing markers characteristic of the pancreatic endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Formation of Cells Expressing Markers Characteristic of the Pancreatic Endocrine Lineage Cells expressing markers characteristic of the pancreatic endoderm lineage may be differentiated into cells expressing markers characteristic of the pancreatic endocrine lineage by any method in the art or by any method disclosed in this invention.

For example, cells expressing markers characteristic of the pancreatic endoderm lineage may be differentiated into cells expressing markers characteristic of the pancreatic endocrine lineage according to the methods disclosed in D'Amour et al, Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4, then removing the medium containing DAPT and exendin 4 and subsequently culturing the cells in medium containing exendin 1, IGF-1 and HGF. An example of this method is disclosed in Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4, then removing the medium containing exendin 4 and subsequently culturing the cells in medium containing exendin 1, IGF-1 and HGF. An example of this method is disclosed in D'Amour et al, Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4. An example of this method is disclosed in D'Amour et al, Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4. An example of this method is disclosed in D'Amour et al, Nature Biotechnology, 2006.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/736,908, assigned to LifeScan, Inc.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/779,311, assigned to LifeScan, Inc.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 60/953,178, assigned to LifeScan, Inc.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage according to the methods disclosed in U.S. patent application Ser. No. 60/990,529.

In one aspect of the present invention, the present invention provides a method for increasing the expression of markers associated with the pancreatic endocrine lineage comprising treating cells expressing markers characteristic of the pancreatic endocrine lineage with medium comprising a sufficient amount of a TGF-β receptor agonist to cause an increase in expression of markers associated with the pancreatic endocrine lineage according to the methods disclosed in U.S. patent application Ser. No. 61/110,278.

Detection of Cells Expressing Markers Characteristic of the Pancreatic Endocrine Lineage Markers characteristic of cells of the pancreatic endocrine lineage are well known to those skilled in the art, and additional markers characteristic of the pancreatic endocrine lineage continue to be identified. These markers can be used to confirm that the cells treated in accordance with the present invention have differentiated to acquire the properties characteristic of the pancreatic endocrine lineage. Pancreatic endocrine lineage specific markers include the expression of one or more transcription factors such as, for example, NGN3, NEUROD, or ISL1.

Markers characteristic of cells of the β cell lineage are well known to those skilled in the art, and additional markers characteristic of the β cell lineage continue to be identified. These markers can be used to confirm that the cells treated in accordance with the present invention have differentiated to acquire the properties characteristic of the β-cell lineage. β cell lineage specific characteristics include the expression of one or more transcription factors such as, for example, PDX1, NKX2.2, NKX6.1, ISL1, PAX6, PAX4, NEUROD, HNF1 beta, HNF6, HNF3 beta, or MAFA, among others. These transcription factors are well established in the art for identification of endocrine cells. See, e.g., Edlund (Nature Reviews Genetics 3: 524-632 (2002)).

The efficiency of differentiation may be determined by exposing a treated cell population to an agent (such as an antibody) that specifically recognizes a protein marker expressed by cells expressing markers characteristic of the pancreatic endocrine lineage. Alternatively, the efficiency of differentiation may be determined by exposing a treated cell population to an agent (such as an antibody) that specifically recognizes a protein marker expressed by cells expressing markers characteristic of the β cell lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

In one aspect of the present invention, the efficiency of differentiation is determined by measuring the percentage of insulin positive cells in a given cell culture following treatment. In one embodiment, the methods of the present invention produce about 100% insulin positive cells in a given culture. In an alternate embodiment, the methods of the present invention produce about 90% insulin positive cells in a given culture. In an alternate embodiment, the methods of the present invention produce about 80% insulin positive cells in a given culture. In an alternate embodiment, the methods of the present invention produce about 70% insulin positive cells in a given culture. In an alternate embodiment, the methods of the present invention produce about 60% insulin positive cells in a given culture. In an alternate embodiment, the methods of the present invention produce about 50% insulin positive cells in a given culture. In an alternate embodiment, the methods of the present invention produce about 40% insulin positive cells in a given culture. In an alternate embodiment, the methods of the present invention produce about 30% insulin positive cells in a given culture. In an alternate embodiment, the methods of the present invention produce about 20% insulin positive cells in a given culture. In an alternate embodiment, the methods of the present invention produce about 10% insulin positive cells in a given culture. In an alternate embodiment, the methods of the present invention produce about 5% insulin positive cells in a given culture.

In one aspect of the present invention, the efficiency of differentiation is determined by measuring glucose-stimulated insulin secretion, as detected by measuring the amount of C-peptide released by the cells. In one embodiment, cells produced by the methods of the present invention produce about 1000 ng C-peptide/pg DNA. In an alternate embodiment, cells produced by the methods of the present invention produce about 900 ng C-peptide/pg DNA. In an alternate embodiment, cells produced by the methods of the present invention produce about 800 ng C-peptide/pg DNA. In an alternate embodiment, cells produced by the methods of the present invention produce about 700 ng C-peptide/pg DNA. In an alternate embodiment, cells produced by the methods of the present invention produce about 600 ng C-peptide/pg DNA. In an alternate embodiment, cells produced by the methods of the present invention produce about 500 ng C-peptide/pg DNA. In an alternate embodiment, cells produced by the methods of the present invention produce about 400 ng C-peptide/pg DNA. In an alternate embodiment, cells produced by the methods of the present invention produce about 500 ng C-peptide/pg DNA. In an alternate embodiment, cells produced by the methods of the present invention produce about 400 ng C-peptide/pg DNA. In an alternate embodiment, cells produced by the methods of the present invention produce about 300 ng C-peptide/pg DNA. In an alternate embodiment, cells produced by the methods of the present invention produce about 200 ng C-peptide/pg DNA. In an alternate embodiment, cells produced by the methods of the present invention produce about 100 ng C-peptide/pg DNA. In an alternate embodiment, cells produced by the methods of the present invention produce about 90 ng C-peptide/pg DNA. In an alternate embodiment, cells produced by the methods of the present invention produce about 80 ng C-peptide/pg DNA. In an alternate embodiment, cells produced by the methods of the present invention produce about 70 ng C-peptide/pg DNA. In an alternate embodiment, cells produced by the methods of the present invention produce about 60 ng C-peptide/pg DNA. In an alternate embodiment, cells produced by the methods of the present invention produce about 50 ng C-peptide/pg DNA. In an alternate embodiment, cells produced by the methods of the present invention produce about 40 ng C-peptide/pg DNA. In an alternate embodiment, cells produced by the methods of the present invention produce about 30 ng C-peptide/pg DNA. In an alternate embodiment, cells produced by the methods of the present invention produce about 20 ng C-peptide/pg DNA. In an alternate embodiment, cells produced by the methods of the present invention produce about 10 ng C-peptide/pg DNA.

Increasing Expression of MAFA in Cells Expressing Markers Characteristic of the Pancreatic Endocrine Lineage In one embodiment, the present invention provides a method for increasing the expression of MAFA in cells expressing markers characteristic of the pancreatic endocrine lineage comprising the steps of culturing the cells expressing markers characteristic of the pancreatic endocrine lineage in medium comprising a sufficient amount of a cyclin-dependent kinase inhibitor to cause an increase in expression of MAFA.

The cyclin-dependent kinase inhibitor may inhibit cyclin-dependent kinase 1. Alternatively, the cyclin-dependent kinase inhibitor may inhibit cyclin-dependent kinase 2. Alternatively, the cyclin-dependent kinase inhibitor may inhibit cyclin-dependent kinase 4. Alternatively, the cyclin-dependent kinase inhibitor may inhibit cyclin-dependent kinase 5. Alternatively, the cyclin-dependent kinase inhibitor may inhibit cyclin-dependent kinase 9. Alternatively, the cyclin-dependent kinase inhibitor may inhibit multiple isoforms of cyclin-dependent kinase, in any combination thereof.

The cyclin-dependent kinase inhibitor may be a protein. Alternatively, the cyclin-dependent kinase inhibitor may be a peptide. Alternatively, the cyclin-dependent kinase inhibitor may be a small molecule. In one embodiment, the small molecule cyclin-dependent kinase inhibitor is selected from the group consisting of 7-n-Butyl-6-(4-hydroxyphenyl)[5H] pyrrolo[2,3-b]pyrazine, 9-Nitro-7,12-dihydroindolo[3,2-d][1]benzazepin-6(5H)-one, 3-(6-Oxo-9-nitro-5,6,7,12-tetrahydroindolo[3,2-d][1]benzazepin-2-yl)propionitrile, (2R)-2-((6-((3-Amino-5-chlorophenyl)amino)-9-(1-methylethyl)-9H-purin-2-yl)amino)-3-methyl-1-butanol, Arcyriaflavin A, [6-Benzylamino-2-(3-hydroxypropylamino)-9-isopropylpurine, Butyrolactone I, (Z)-1-(3-Ethyl-5-methoxy-2,3-dihydrobenzothiazol-2-ylidene)propan-2-one, 2-(3-Hydroxypropylamino)-6-(o-hydroxybenzylamino)-9-isopropylpurine, 1-(2,6-Dichlorophenyl)-1,5-dihydro-6-((4-(2-hydroxyethoxy)phenyl)methyl)-3-(1-methylethyl)-4H-pyrazolo[3,4-d]pyrimidin-4-one, Cdk/Cyclin Inhibitory Peptide III, 3-(2-Chloro-3-indolylmethylene)-1,3-dihydroindol-2-one, Ethyl-(6-hydroxy-4-phenylbenzo[4,5]furo[2,3-b])pyridine-3-carboxylate, RO-3306, N-(cis-2-Aminocyclohexyl)-N-(3-chlorophenyl)-9-ethyl-9H-purine-2,6-diamine, 6-Cyclohexylmethoxy-2-(4'-sulfamoylanilino)purine, 5-Amino-3-((4-(aminosulfonyl)phenyl)amino)-N-(2,6-difluorophenyl)-1H-1,2,4-triazole-1-carbothioamide, 3-Amino-1H-pyrazolo[3,4-b]quinoxaline, Cdk2 Inhibitor I, Cdk2 Inhibitor II, 2(bis-(Hydroxyethyl)amino)-6-(4-methoxybenzylamino)-9-isopropylpurine, 4-(6-Cyclohexylmethoxy-9H-purin-2-ylamino)-N,N-diethylbenzamide, N4-(6-Aminopyrimidin-4-yl)-sulfanilamide, (4-(2-Amino-4-methylthiazol-5-yl)pyrimidin-2-yl)-(3-nitrophenyl)amine, 2-Bromo-12,13-dihydro-5H-indolo[2,3-a]pyrrolo[3,4-c]carbazole-5,7(6H)-dione, 1,4-Dimethoxyacridine-9(10H)-thione, 5-(N-(4-Methylphenyl)amino)-2-methyl-4,7-dioxobenzothiazole, 4-(3,5-Diamino-1Hpyrazol-4-ylazo)-phenol, 2-(2-Hydroxyethylamino)-6-(3-chloroanilino)-9-isopropylpurine, Fascaplysin, Indirubin-3'-monoxime, Indirubin-3'-monoxime, 5-Iodo-, Indirubin-3'-monoxime-5-sulphonic Acid, Isogranulatimide, 2-(2-Hydroxyethylamino)-6-benzylamino-9-methylpurine, 6-(2-Hydroxybenzylamino)-2-((1R)-(hydroxymethyl)propyl)amino)-9-isopropylpurine, 5-Bromo-3-(2-(4-Fluorophenyl)-2-oxoethylidine)-1,3-dihydroindol-2-one, N6,N6-Dimethyladenine, 2-(1R-Isopropyl-2-hydroxyethylamino)-6-(3-chloroanilino)-9-isopropyl-purine, rapamycin, 2-(R)-(1-Ethyl-2-hydroxyethylamino)-6-benzylamino-9-isopropylpurine, Scytonemin, 3-[1-(3H-Imidazol-4-yl)-meth-(Z)-ylidene]-5-methoxy-1,3-dihydroindol-2-one, and 4-(3'-Hydroxyphenyl)amino-6,7-dimethoxyquinazoline.

In one embodiment, the cyclin-dependent kinase inhibitor is ethyl-(6-hydroxy-4-phenylbenzo[4,5]furo[2,3-b])pyridine-3-carboxylate. In one embodiment, ethyl-(6-hydroxy-4-phenylbenzo[4,5]furo[2,3-b])pyridine-3-carboxylate is added to cells expressing markers characteristic of the endocrine lineage at a concentration from about 0.1 µM to about 10 µM for about one to seven days.

In one embodiment, cells expressing markers characteristic of the endocrine lineage are treated with ethyl-(6-hydroxy-4-phenylbenzo[4,5]furo[2,3-b])pyridine-3-carboxylate for about one to about seven days.

The present invention is further illustrated, but not limited by, the following examples.

EXAMPLES

Example 1

Differentiation of Human Embryonic Stem Cells of the Cell Line H1 to Pancreatic Endocrine Cells in the Absence of Fetal Bovine Serum Cells of the human embryonic stem cells line H1 at passage 52 were cultured on MATRIGEL®-coated dishes (1:30 dilution) and exposed to the following differentiation protocol, in order to differentiate the cells to cells expressing markers characteristic of the pancreatic endocrine lineage.

a. RPMI medium supplemented with 2% BSA (Catalog #152401, MP Biomedical, Ohio), and 100 ng/ml activin A (R&D Systems, MN) plus 20 ng/ml WNT-3a (Catalog #1324-WN-002, R&D Systems, MN) plus 8 ng/ml of bFGF (Catalog #100-18B, PeproTech, NJ), for one day followed by treatment with RPMI media supplemented with 2% BSA and 100 ng/ml activin A plus 8 ng/ml of bFGF for an additional two days (Stage 1), then b. DMEM/F12+2% BSA+50 ng/ml FGF7+0.25 µM Cyclopamine-KAAD (#239804, Calbiochem, CA) for two days (Stage 2), then c. DMEM/F12+1% B27 (Invitrogen, CA)+50 ng/ml FGF7+0.25 µM Cyclopamine-KAAD+2 µM Retinoic acid (RA) (Sigma, MO)+100 ng/ml of Noggin (R & D Systems, MN) for four days (Stage 3), then d. DMEM/F12+1% B27 (Invitrogen, CA)+100 ng/ml Noggin+1 µM DAPT (a gamma-secretase inhibitor) (Catalog #565784, Calbiochem, CA)+1 µM ALK5 inhibitor II (Catalog #616452, Calbiochem, Ca)+100 ng/ml of Netrin-4 (R&D Systems, MN) for three days (Stage 4), then e. DMEM/F12+1% B27 (Invitrogen, CA)+1 µM ALK5 inhibitor II (Calbiochem, Ca) for seven days (Stage 5).

Medium was changed daily. At each stage the cell number was calculated using a hemocytometer and RNA was collected for PCR analysis. All samples were collected in triplicate.

Example 2

Screening of the Effects of Compounds from the EMD Kinase Inhibitor Library II on Cells that have been Treated According to the Differentiation Protocol Outlined in Example 1

Cells of the human embryonic stem cell line H1 at passage 44 were seeded onto MATRIGEL™ coated 24-well dishes (1:30 dilution), and differentiated according to the methods described in Example 1 up to stage 5. Following this, the cells were treated for four days in DMEM/F12+1% B27 containing a compound from an EMD Calbiochem compound library (Catalog #539745, Calbiochem, San Diego, Calif.) at a final concentration of 1 µM. Wells containing vehicle were included as a control. Throughout the protocol media was changed daily. All samples were treated in duplicate. At the completion of this treatment RNA was collected for PCR analysis. Samples were analyzed by real-time PCR for expression of insulin, glucagon, MAFA, and Arx4. Results are expressed as a ratio insulin/glucagon (FIG. 1A), or MAFA versus ARX4 (FIG. 1B) of the treated samples relative to the untreated control, as measured by real-time PCR. The corresponding PubChem Compound ID# for each well # is listed in Table 1.

Treatment of cells expressing markers characteristic of the pancreatic endocrine lineage with compounds A6, B7, B8, or C2 at a 1 µM concentration resulted in an insulin/glucagon expression ratio of approximately 3.0 or higher (see FIG. 1A).

We next examined the effect of these compounds on the ratio of MAFA/ARX4, and we observed that treatment of cells expressing markers characteristic of the pancreatic endocrine lineage with several of the compounds resulted in a much greater change in the ratio of MAFA to ARX4 than other compounds tested in the library: Cells treated with compound B8 showed a ratio of MAFA/ARX4 of approximately 1000. Treatment of cells expressing markers characteristic of the pancreatic endocrine lineage with compound C2 resulted in a MAFA/ARX4 ratio of approximately 100. (See FIG. 1B).

Example 3

The Effects of Cyclin-Dependent Kinase Inhibitor Treatment on Insulin and MAFA Expression in Cells that have been Treated According to the Differentiation Protocol Outlined in Example 1

Several of the compounds that increased the ratio of insulin to glucagon expression, or MAFA to ARX4 expression in Example 2 were cyclin-dependent kinase inhibitors. One such compound was PubChem Compound ID #5330797 (5-Amino-3-((4-(aminosulfonyl)phenyl)amino)-N-(2,6-difluorophenyl)-1H-1,2,4-triazole-1-carbothioamide) (Catalogue #217714; Calbiochem, San Diego, Calif.). To confirm these observations, cells of the human embryonic stem cell line H1 at passage 42 were cultured in 10 cm$^2$ MATRIGEL®-coated dishes and treated according to the methods described in Example 1 up to stage 5. After stage 5, the cells were treated with DMEM/F12 containing 1% B27 containing 1 µM PubChem Compound ID #5330797 for six days. Medium was changed every other day. Samples of cells were taken for real-time PCR prior to treatment with the compound, and at days two and five of compound treatment.

Figure 2C:
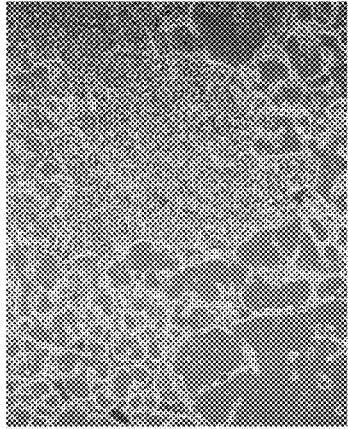
FIG. 2C shows a 4× micrograph of cells treated with 1 µM of the compound PubChemID #5330812 at day 4 of treatment.
Figure 2F:
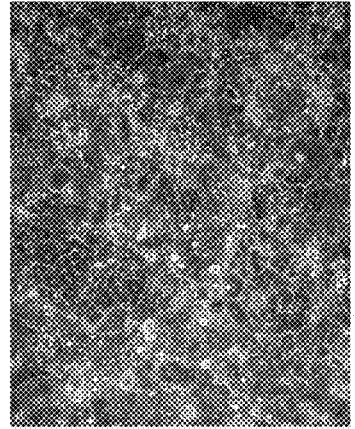
FIG. 2F shows a 20× micrograph of cells treated with 1 µM of the compound PubChemID #5330812 at day 6 of treatment.
Figure 2B:
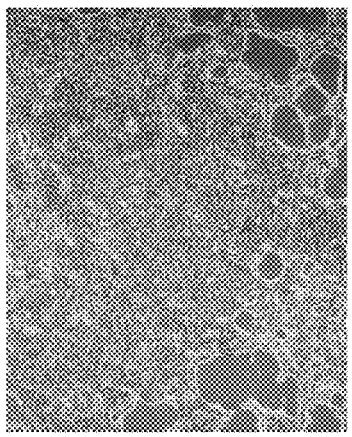
FIG. 2B shows a 4× micrograph of cells treated with 0.5 µM of the compound PubChemID #5330812 at day 4 of treatment.
Figure 2E:
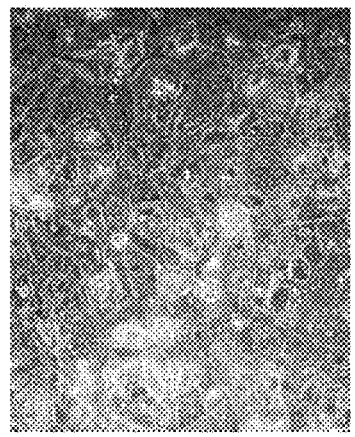
FIG. 2E shows a 20× micrograph of cells treated with 0.5 µM of the compound PubChemID #5330812 at day 6 of treatment.
Figure 2A:
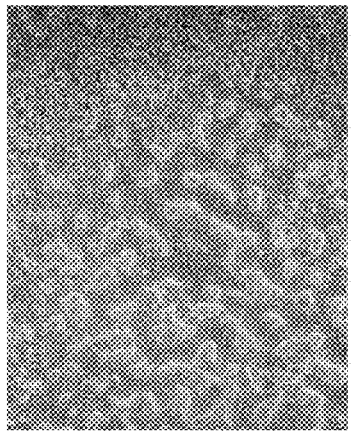
FIG. 2A shows a 4× micrograph of cells treated according to the methods described in Example 1, at day 4 of the stage 6 treatment.
Figure 2D:
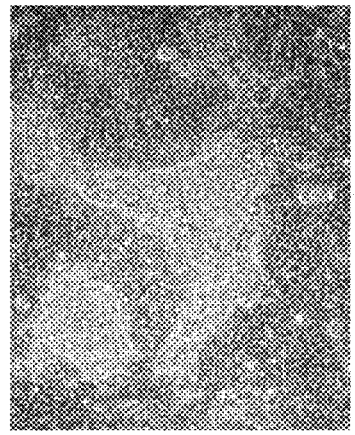
FIG. 2D shows a 20× micrograph of cells treated according to the methods described in Example 1, at day 6 of the stage 6 treatment.

Characteristic micrographs of the cells at day 4 or day 6 of compound treatment versus untreated controls are shown in FIGS. 2A-2F. Untreated cells are highly packed (FIGS. 2A and 2D) and it is difficult to distinguish individual cells. However, after treatment with 0.5 µM or 1 µM of PubChem Compound ID #5330797 for six days, individual nuclei became visible (FIGS. 2E and 2F) as compared to the untreated control (FIG. 2D), indicating that there was differentiation occurring in the cell population. This was also accompanied by some cell death, which can be seen by gaps in the layer of cells as shown in FIGS. 2B and 2C.

Figure 3A:
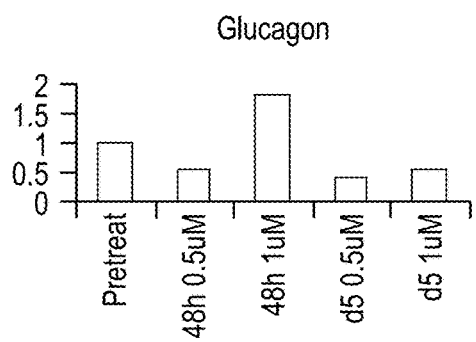
FIGS. 3A-W show the expression of the 23 genes indicated, in cells expressing markers characteristic of the pancreatic endocrine lineage following a five-day treatment of 0.5 µM (dark bars) or 1.0 µM (light bars) of the compound PubChem ID #5330812. Expression levels were determined at day 0, day 2 and day 5.

Treatment of cells with PubChem Compound ID #5330797 resulted in the increase in expression of insulin, glucagon, MAFA, MAFB and somatostatin, albeit to differing degrees. The relative induction of gene expression per treatment as compared to day 0 (pretreatment) cultures is shown in FIGS. 3A-3V. Cells expressing markers characteristic of the pancreatic endocrine lineage that were treated with 1 µM PubChem Compound ID #5330797 resulted in an approximately 1.5 fold increase in glucagon expression at 48 hrs of treatment. This expression declined to below pretreatment levels after 5 days of treatment. No increase in glucagon expression was observed with treatment of 0.5 µM PubChem Compound ID #5330797. (See FIG. 3A).

Figure 3B:
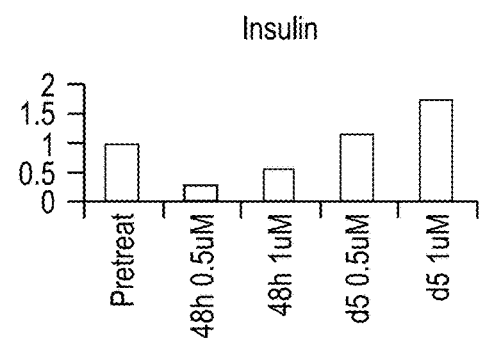

Cells expressing markers characteristic of the pancreatic endocrine lineage that were treated with 1 µM PubChem Compound ID #5330797 for five days resulted in an approximately 1.5 fold increase in insulin expression. (See FIG. 3B).

Figure 3C:
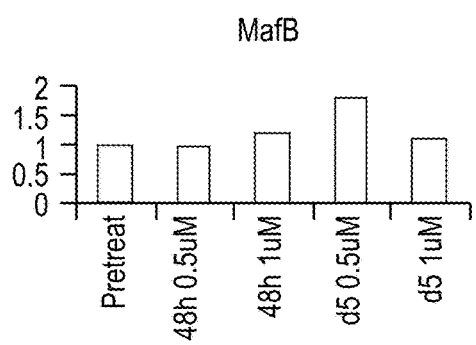
Figure 3D:
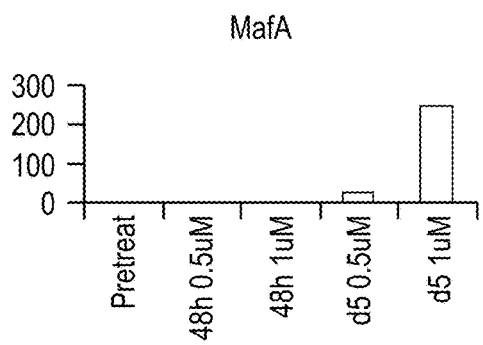

Cells expressing markers characteristic of the pancreatic endocrine lineage that were treated with 1 µM PubChem Compound ID #5330797 for five days resulted in an approximately 200 fold increase in MAFA expression. (See FIG. 3D).

Figure 3E:
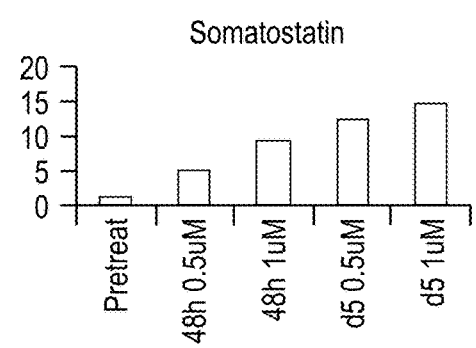

Cells expressing markers characteristic of the pancreatic endocrine lineage that were treated with 0.5 µM PubChem Compound ID #5330797 for five days resulted in an approximately 1.5 fold increase in MAFB expression. (See FIG. 3C). A dose-dependent increase in the expression of somatostatin was observed (FIG. 3E).

Figure 3F:
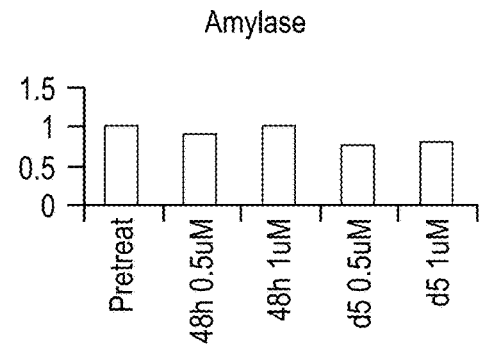
Figure 3G:
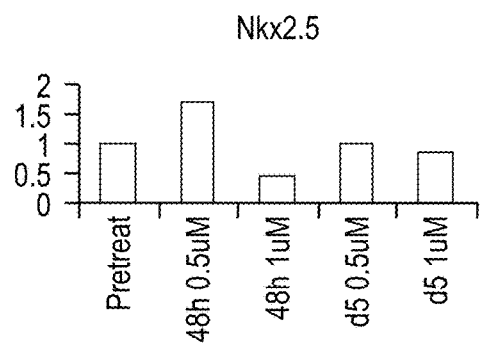
Figure 3H:
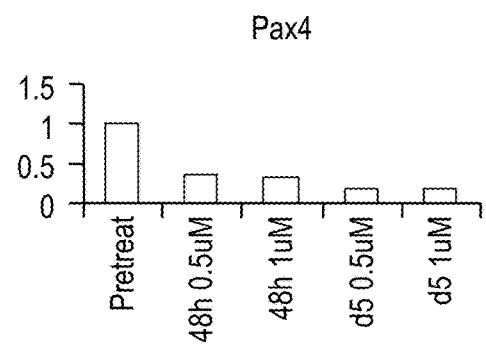
Figure 3I:
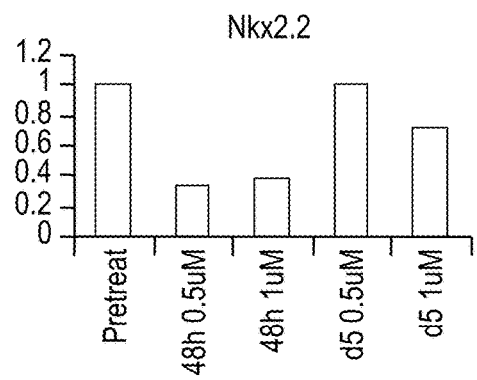
Figure 3J:
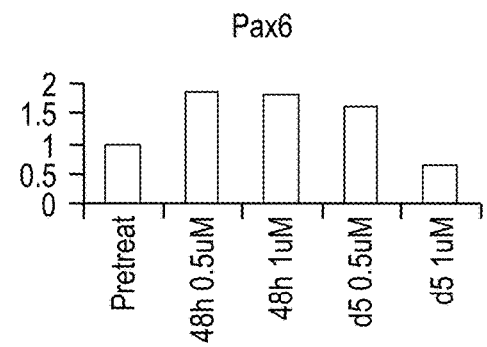
Figure 3K:
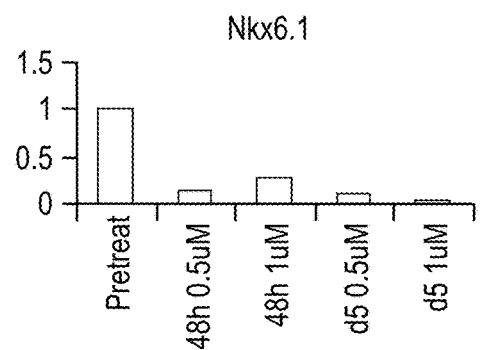
Figure 3L:
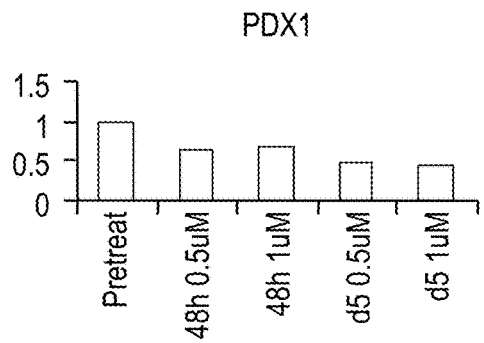
Figure 3M:
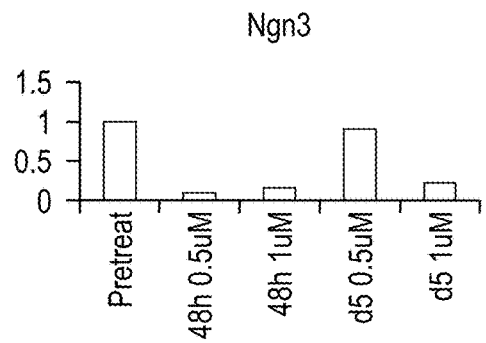
Figure 3N:
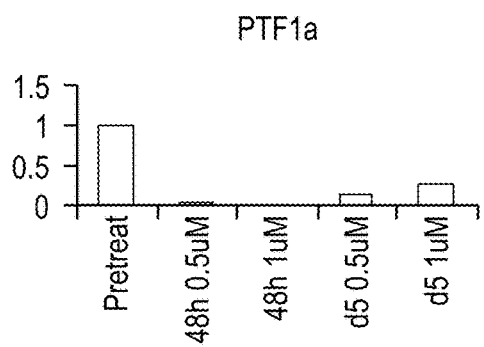
Figure 3O:
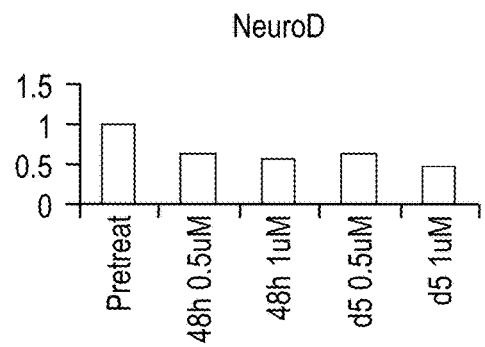
Figure 3P:
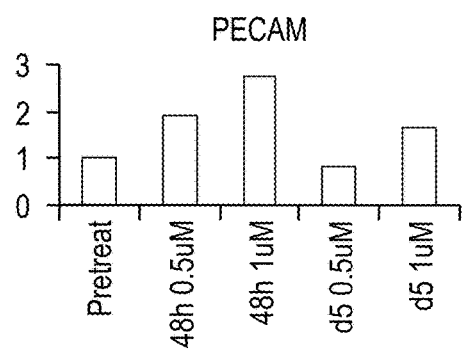
Figure 3Q:
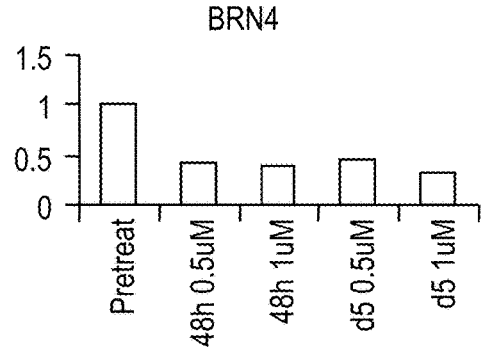
Figure 4E:
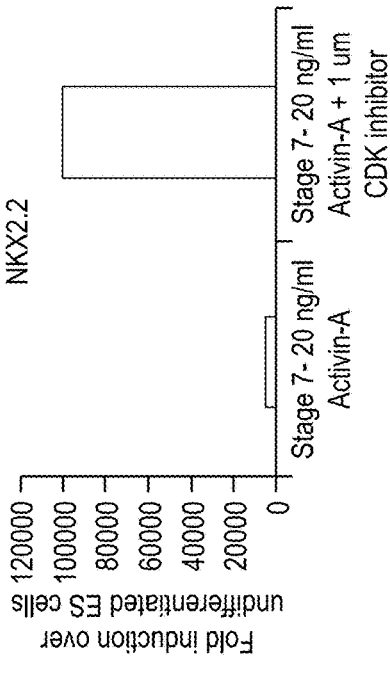
Figure 4F:
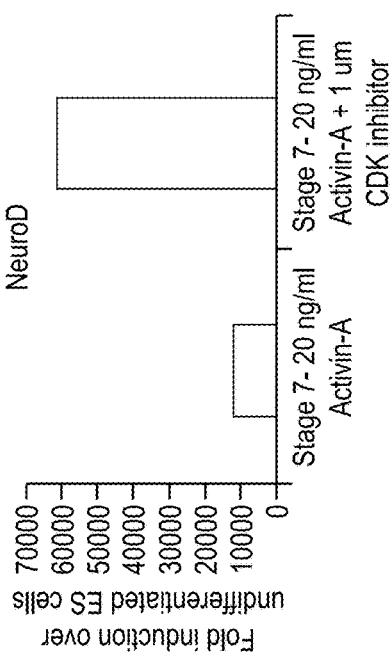
Figure 4G:
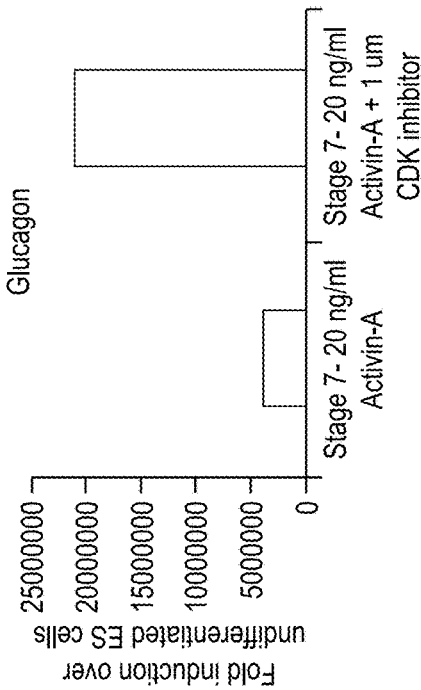
Figure 4H:
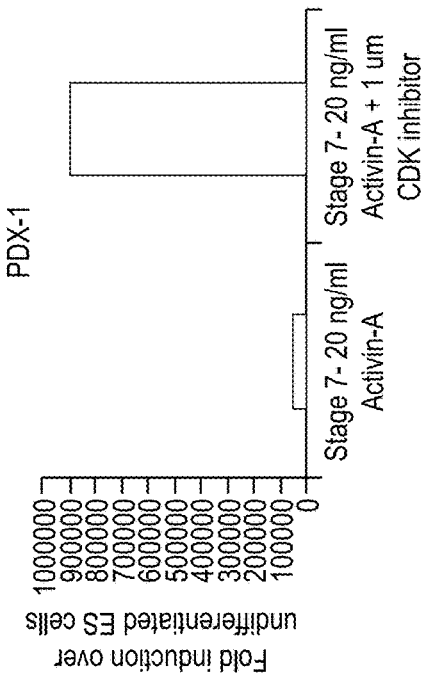
Figure 4I:
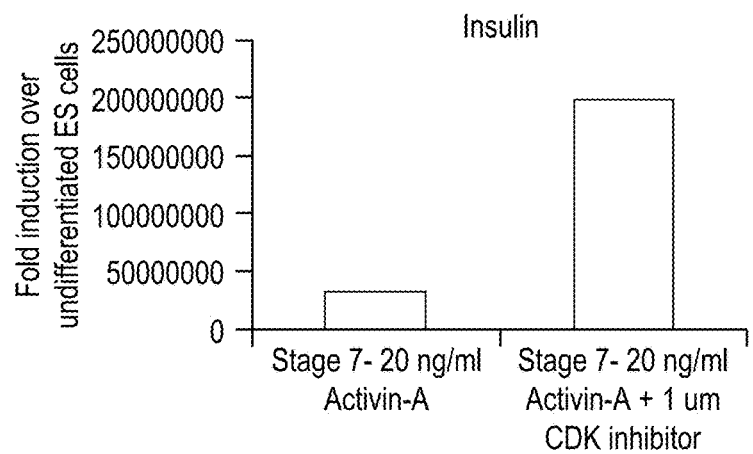

No change in the expression of amylase was observed in cells expressing markers characteristic of the pancreatic endocrine lineage that were treated with PubChem Compound ID #5330797 for five days. (See FIG. 3F). However, decreases in the level of expression of PAX4 (FIG. 3H), NKX6.1 (FIG. 3K), PDX1 (FIG. 3L), NEUROD (FIG. 3O), and BRN4 (FIG. 3Q) was observed.

Example 4

Cyclin-Dependent Kinase Inhibitor Treatment Increased the Expression of MAFA in Islet-Like Clusters Cells of the human embryonic stem cell line H1 at passage 52 were cultured on MATRIGEL® coated dishes (1:30 dilution) and differentiated according to the methods described in Example 1. An additional stage (Stage 6) was added, in order to further mature the cells expressing markers characteristic of the pancreatic endocrine lineage. Stage 6 in this example consisted of a seven day treatment in DMEM/F12+1% B27 (Invitrogen, CA). The medium was changed daily.

After stage 6, the cells were treated for 5 mins at room temperature with 1× accutase (Sigma, MO). The accutase was removed, and DMEM/12+1% B27 was added to the cells. The attached cells were removed using a cell scarper and gently resuspended and passed through a 40 µm cell strainer. The cells retained on the strainer were removed by rinsing in basal media and cultured in suspension on Ultra-Low culture plates (Catalogue #3471, Corning, Ma). The cells were then treated as follows: The cells were cultured in DMEM/F12+1% B27, containing 20 ng/ml of activin A (AA), 1 µm of CDK inhibitor III (Catalog #217714, Calbiochem, Ca) for 10 days (Stage 7). Cells treated with vehicle were included as controls. Samples were collected at days 7 through 10 for PCR analysis and dithizone staining. The cells cultured in suspension according to the methods outlined in this example assumed a morphology similar to pancreatic islet clusters. Treatment with CDK inhibitor III did not appear to affect the morphology of the islet like clusters.

FIGS. 4A-4I show the effect of CDK inhibitor III treatment on gene expression profile of the cell clusters. Treatment with of CDK inhibitor III increased the expression of markers associated with the pancreatic endocrine lineage and in particular increased the expression of the pro-insulin transcription factor, MAFA.

Figure 5A:
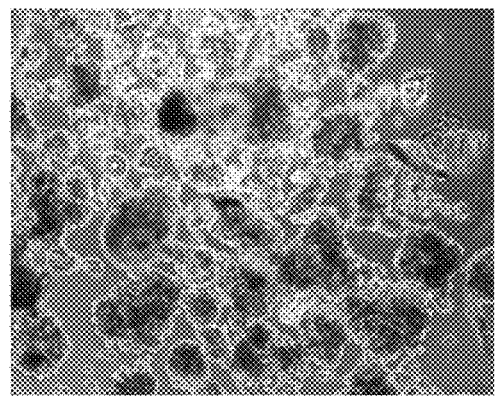
FIGS. 5A and 5B show the effect of CDK inhibitor III treatment on the dithazone staining of islet-like clusters.
Figure 5B:
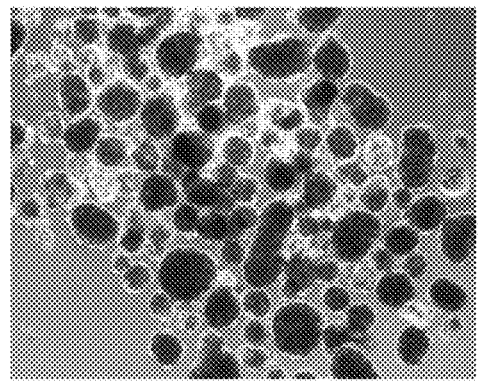

FIGS. 5A-5B show the effect of CDK inhibitor III on dithazone (DTZ) staining of clusters. Cell clusters treated with CDK inhibitor and stained with DTZ, showed a more reddish staining pattern as compared to clusters not treated with the CDK inhibitor III.

Example 5

FACS Analysis of Insulin Producing Cells Produced by the Methods of the Present Invention Cells of the human embryonic stem cell line H1 at passage 42 were cultured on MATRIGEL®-coated plates, and differentiated into insulin producing cells using the following protocol:

a. RPMI medium supplemented with 2% BSA (Catalog #152401, MP Biomedical, Ohio), and 100 ng/ml activin A (R&D Systems, MN) plus 20 ng/ml WNT-3a (Catalog #1324-WN-002, R&D Systems, MN) plus 8 ng/ml of bFGF (Catalog #100-18B, PeproTech, NJ), for one day followed by treatment with RPMI media supplemented with 2% BSA and 100 ng/ml activin A plus 8 ng/ml of bFGF for an additional two days (Stage 1), then b. DMEM/F12+2% BSA+50 ng/ml FGF7+0.25 µM Cyclopamine-KAAD (#239804, Calbiochem, CA) for two days (Stage 2), then c. DMEM/F12+1% B27 (Invitrogen, CA)+50 ng/ml FGF7+0.25 µM Cyclopamine-KAAD+2 µM Retinoic acid (RA) (Sigma, MO)+100 ng/ml of Noggin (R & D Systems, MN) for four days (Stage 3), then d. DMEM/F12+1% B27 (Invitrogen, CA)+100 ng/ml Noggin+1 µM DAPT (a gamma-secretase inhibitor) (Catalog #565784, Calbiochem, CA)+1 µM ALK5 inhibitor II (Catalog #616452, Calbiochem, Ca)+100 ng/ml of Netrin-4 (R&D Systems, MN) for three days (Stage 4), then e. DMEM/F12+1% B27 (Invitrogen, CA)+1 µM ALK5 inhibitor II (Calbiochem, Ca) for seven days (Stage 5), then f. DMEM/F12+1% B27 for seven days (Stage 6), then g. Treatment with Accutase for 5 minutes, followed by scraping to remove any remaining attached cells. The cell suspension was then passed through a 40 µm cell strainer. The cells retained on the strainer were removed by rinsing in basal media and cultured in suspension on Ultra-Low culture plates in DMEM-High Glucose (Catalogue #11995-073, Invitrogen, Ca)+1% B27+20 ng/ml of activin A (AA) 1 µm of CDK inhibitor III (Catalog #217714, Calbiochem, Ca) for 5 days (Stage 7).

Islet-like clusters were dispersed into single cells using TrypLE Express (Invitrogen, Carlsbad, Calif.) and washed in cold PBS. For fixation, the cells were resuspended in 200-300 µl Cytofix/Cytoperm Buffer (BD 554722, BD, Ca) and incubated for 30 min at 4° C. Cells were washed two times in 1 ml Perm/Wash Buffer Solution (BD 554723) and resuspended in 100 µl staining/blocking solution containing 2% normal goat serum in Perm/Wash buffer. For flow cytometric analysis, cells were stained with the following primary antibodies: Anti-Insulin (Rabbit mAb, Cell Signaling No. C27C9; 1:100 dilution); Anti-Glucagon (Mouse Mab, Sigma No. G2654, 1:100); Anti-Synaptophysin (Rabbit Polyclonal antibody, DakoCytomation No A0010, 1:50). Cells were incubated for 30 min at 4° C. followed by two washes in Perm/Wash buffer and a further 30 min incubation in appropriate secondary antibodies as follows: Goat anti-Rabbit Alexa 647 (Invitrogen No. A21246) or Goat anti-Mouse 647 (Invitrogen No. A21235); Goat anti-Rabbit R-PE (BioSource No. ALI4407). All secondary antibodies were used at a 1:200 dilution. Cells were washed at least once in Perm/Wash buffer and analyzed using BD FACSArray. At least 10,000 events were acquired for analysis. Controls included undifferentiated H1 cells and the β-TC (CRL-11506™ ATCC, VA) cell line.

Figure 6C:
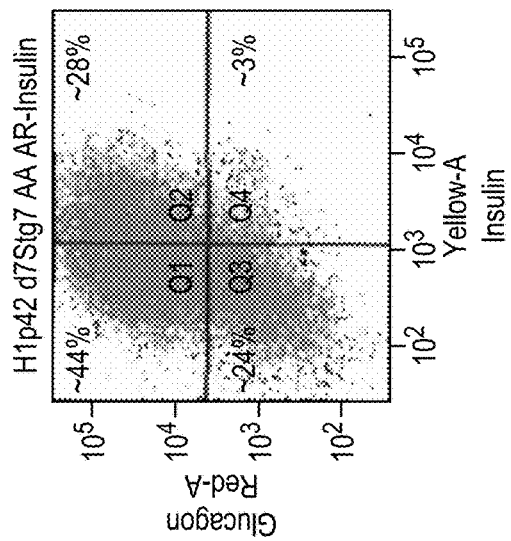
FIGS. 6A-C show the expression of insulin, synaptophysin and glucagon in insulin-producing cells produced according to the methods described in Example 5. Expression of the proteins indicated was determined by FACS.
Figure 6B:
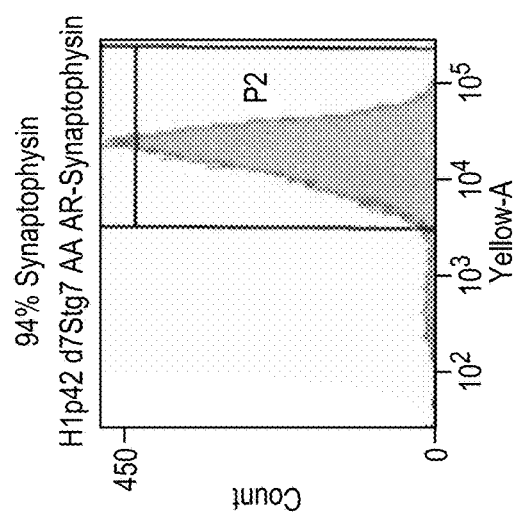
Figure 6A:
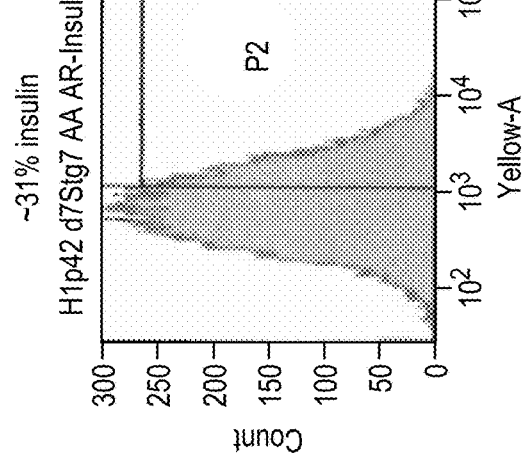

FIGS. 6A-6C show the percentage insulin positive, synaptophysin positive, and glucagon positive cells in cells following treatment with Stage 7, in medium containing vehicle. FIGS. 7A-7C show the percentage insulin positive, synaptophysin positive, and glucagon positive cells following treatment with Stage 7 in medium containing 1 µM CDK inhibitor III for 5 days. The number of single hormonal insulin positive cells increased from 3% to 8% following treatment with the CDK inhibitor. Additionally, the percentage of poly hormonal (insulin and glucagon positive) cells decreased following treatment with the CDK inhibitor.

Example 6

Kinetics of CDK Inhibitor-Induced MAFA Expression

Cells of the human embryonic stem cell line H1 at passage 42 were cultured on MATRIGEL®-coated plates, and differentiated into insulin producing cells using the following protocol:

a. RPMI medium supplemented with 2% BSA (Catalog #152401, MP Biomedical, Ohio), and 100 ng/ml activin A (R&D Systems, MN) plus 20 ng/ml WNT-3a (Catalog #1324-WN-002, R&D Systems, MN) plus 8 ng/ml of bFGF (Catalog #100-18B, PeproTech, NJ), for one day followed by treatment with RPMI media supplemented with 2% BSA and 100 ng/ml activin A plus 8 ng/ml of bFGF for an additional two days (Stage 1), then b. DMEM/F12+2% BSA+50 ng/ml FGF7+0.25 µM Cyclopamine-KAAD (#239804, Calbiochem, CA) for two days (Stage 2), then c. DMEM/F12+1% B27 (Invitrogen, CA)+50 ng/ml FGF7+0.25 µM Cyclopamine-KAAD+2 µM Retinoic acid (RA) (Sigma, MO)+100 ng/ml of Noggin (R & D Systems, MN) for four days (Stage 3), then d. DMEM/F12+1% B27 (Invitrogen, CA)+100 ng/ml Noggin+1 µM DAPT (a gamma-secretase inhibitor) (Catalog #565784, Calbiochem, CA)+1 µM ALK5 inhibitor II (Catalog #616452, Calbiochem, Ca)+100 ng/ml of Netrin-4 (R&D Systems, MN) for three days (Stage 4), then e. DMEM/F12+1% B27 (Invitrogen, CA)+1 µM ALK5 inhibitor II (Calbiochem, Ca) for seven days (Stage 5), then f. DMEM/F12+1% B27 for seven days (Stage 6), then g. Treatment with Accutase for 5 minutes, followed by scraping to remove any remaining attached cells. The cell suspension was then passed through a 40 µm cell strainer. The cells retained on the strainer were removed by rinsing in basal media and cultured in suspension on Ultra-Low culture plates in DMEM-High Glucose (Catalogue #11995-073, Invitrogen, Ca)+1% B27+20 ng/ml of activin A (AA) 2 µm of CDK inhibitor III (Catalog #217714, Calbiochem, Ca) for 1-8 days (Stage 7).

Samples were collected for PCR analysis at days 1, 2, 3, and 4. Following 4 days of treatment with CDK inhibitor, the CDK inhibitor was removed from culture and the cells were cultured additional 4 days in DMEM-F12+1% B27+20 ng/ml of activin A. At the end of the four days, samples were collected in triplicate for PCR analysis.

Figure 8A:
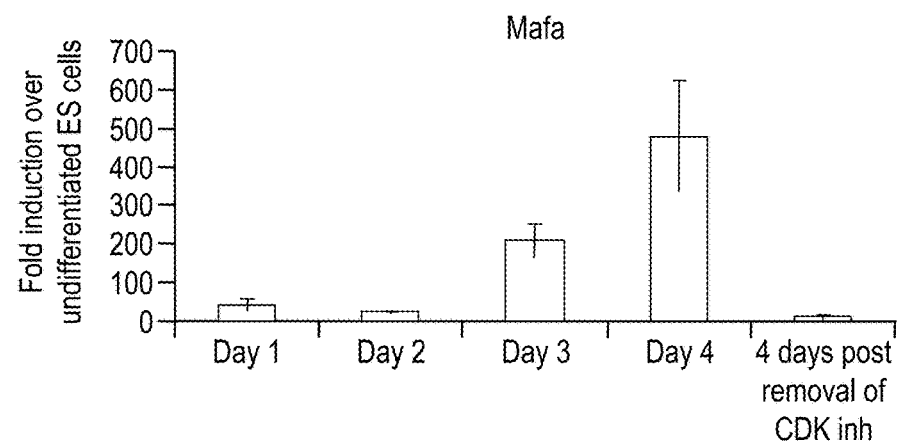
FIGS. 8A and 8B show the expression of MAFA and insulin, respectively, in insulin-producing cells, produced by the methods of the present invention. Samples of cells were taken for PCR analysis at days 1, 2, 3, and 4. Following 4 days of treatment with CDK inhibitor, the CDK inhibitor was removed from culture and the cells were cultured additional 4 days in DMEM-F12+1% B27+20 ng/ml of activin A. At the end of the four days, samples were collected in triplicate for PCR analysis.
Figure 8B:
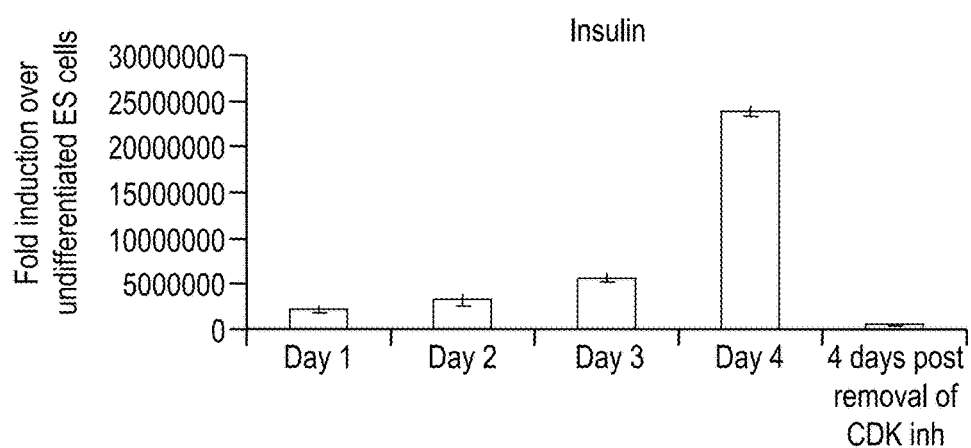

FIGS. 8A-8B show expression pattern of MAFA and insulin at various time points of stage 7. CDK inhibitor treatment resulted in significant increase in MAFA and insulin expression which increased as a function of time. However, removal of CDK inhibitor resulted in a significant drop to both MAFA and insulin expression, in samples obtained four days after removal of the compound.

Example 7

Screening of the Effects of Compounds from the BIOMOL™ Kinase Inhibitor Library on Cells that have been Treated According to the Differentiation Protocol Outlined in Example 1

Cells of the human embryonic stem cell line H1 at passage 51 were seeded onto MATRIGEL®-coated 24-well dishes (1:30 dilution), and differentiated according to the methods described in Example 1 up to stage 5. Following this, the cells were grown for one day in DMEM/F12+1% B27 and then treated for six days in DMEM/F12+1% B27 containing a compound from a BIOMOL™ compound library (Catalog #2832, BIOMOL, Plymouth Meeting, Pa.) at a final concentration of 4 μM. Wells containing vehicle were included as a control. Throughout the treatment protocol media containing vehicle or compound was changed every other day. All samples were treated in duplicate. At the completion of this treatment RNA was collected for PCR analysis. Samples were analyzed by real-time PCR for expression of insulin, glucagon, MAFA, and ARX4. Results are expressed as a ratio insulin/glucagon (Table 2), or MAFA versus Arx4 (Table 2) of the treated samples relative to the untreated control, as measured by real-time PCR. The corresponding catalog#, CAS#, and compound name or ID number for each alpha numeric well# is listed in Table 3.

Treatment of cells expressing markers characteristic of the pancreatic endocrine lineage with compounds C8 or F1 at a 4 μM concentration resulted in an insulin/glucagon expression ratio of approximately 10.0 or higher. Cells treated with D9 had an insulin/glucagon expression ratio of approximately 1840.0 (Table 2).

We next examined the effect of these compounds on the ratio of MAFA/ARX4, and we observed that treatment of cells expressing markers characteristic of the pancreatic endocrine lineage with several of the compounds resulted in a much greater change in the ratio of MAFA to ARX4 than other compounds tested in the library: Cells treated with compound B6 or F1 showed a ratio of MAFA/ARX4 of approximately greater than 10. Treatment of cells expressing markers characteristic of the pancreatic endocrine lineage with compound C8 resulted in a MAFA/ARX4 ratio of approximately 84, while cells treated with D9 had a MAFA/ARX4 ratio of approximately 212. (Table 2).

Example 8

The Effect of Cyclin-Dependent Kinase Inhibitors on Insulin and MAFA Expression in Cells Treated According to the Differentiation Protocol Outlined in Example 1

Cells of the human embryonic stem cell line H1 at passage 51 were seeded onto MATRIGEL™ coated 24-well dishes (1:30 dilution), and differentiated according to the methods described in Example 1 up to stage 5. Following this, the cells were grown for eight days in DMEM/F12+1% B27 and then treated for four days in DMEM/F12+1% B27 containing a cyclin dependent kinase inhibitor at a final concentration of 0.6125, 1.25, or 5.0 μM. We tested 6 inhibitors: PubChem ID #5330812 (EMD cat #217714), PubChem ID #4566 (EMD cat #217713), PubChem ID#5330797 (EMD cat #219476), PubChem ID #73292 (EMD cat #341251), PubChem ID #4592 (EMD cat #495620), and PubChem ID #160355 (EMD cat #557360). Wells containing vehicle were included as a control. Throughout the treatment protocol media containing vehicle or compound was changed every other day. All samples were treated in duplicate. At the completion of this treatment RNA was collected for PCR analysis. Samples were analyzed by real-time PCR for expression of insulin, glucagon, MAFA, and ARX4. Results are expressed as the fold change relative to the vehicle treated control, as measured by real-time PCR.

We observed that the compounds PubChem ID #5330812, PubChem ID #4566, PubChem ID #5330797, and PubChem ID #73292 all stimulated MAFA expression at the concentrations tested (Table 4). PubChem ID #4592 and PubChem ID #160355 did not stimulate MAFA at the concentrations tested (Table 4). The compounds PubChem ID #5330812, PubChem ID #4566, PubChem ID #5330797, PubChem ID #4592 and PubChem ID #160355 all appeared to stimulate insulin expression (Table 4). The compound PubChem ID #5330797 reduced both glucagon and Arx4 expression (Table 4) while stimulating MAFA expression.

Example 9

Differentiation of Human Embryonic Stem Cells of the Cell Line H1 to Pancreatic Endocrine Cells with DMEM Containing 25 mM Glucose (DMEM-HG), Lacking Fetal Bovine Serum Cells of the human embryonic stem cells line H1 were cultured on MATRIGEL®-coated dishes (1:30 dilution) and differentiated into cells expressing markers characteristic of the pancreatic endocrine lineage using the following protocol:

a. RPMI medium supplemented with 2% BSA (Catalog #152401, MP Biomedical, Ohio), and 100 ng/ml activin A (R&D Systems, MN) plus 20 ng/ml WNT-3a (Catalog #1324-WN-002, R&D Systems, MN) plus 8 ng/ml of bFGF (Catalog #100-18B, PeproTech, NJ), for one day followed by treatment with RPMI media supplemented with 2% BSA and 100 ng/ml activin A plus 8 ng/ml of bFGF for an additional two days (Stage 1), then b. RPMI medium supplemented with 2% BSA+50 ng/ml FGF7+0.25 μM Cyclopamine-KAAD (#239804, Calbiochem, CA) for two days (Stage 2), then c. DMEM-HG+1% B27 (Invitrogen, CA)+50 ng/ml FGF7+0.25 μM Cyclopamine-KAAD+2 μM Retinoic acid (RA) (Sigma, MO)+100 ng/ml of Noggin (R & D Systems, MN) for six days (Stage 3), then d. DMEM-HG+1% B27 (Invitrogen, CA)+100 ng/ml Noggin+1 μM ALK5 inhibitor II (Catalog #616452, Calbiochem, Ca) for three days (Stage 4), then e. DMEM-HG+1% B27 (Invitrogen, CA)+1 μM ALK5 inhibitor II (Calbiochem, Ca) for seven days (Stage 5).

Medium was changed daily. At each stage the cell number was calculated using a hemocytometer and RNA was collected for PCR analysis. All samples were collected in triplicate.

Example 10

Screening of the Effects of Compounds from the EMD Kinase Inhibitor Library I on Cells Treated According to the Differentiation Protocol Outlined in Example 9

Cells of the human embryonic stem cell line H1 at passage 45 were seeded onto MATRIGEL®-coated 24-well dishes (1:30 dilution), and differentiated according to the methods described in Example 9 up to stage 5. Following this, the cells were fed and treated on day 1, 3, and 5 of stage 5 with media comprising DMEM-HG, 1% B27 (Invitrogen, CA), 1 μM ALK5 inhibitor II (Caibiochem, Ca) and a compound from an EMD Calbiochem compound library 1 solubilized in DMSO (Catalog #539744, Calbiochem, San Diego, Calif.) and treated at a final concentration of 2.5 μM. Wells containing vehicle were included as a control. Throughout the protocol media was changed daily except at stage 5 when media was changed every other day. All samples were treated in duplicate.

At the completion of this treatment RNA was collected for PCR analysis. Samples were analyzed by real-time PCR for expression of MAFA. Results are expressed as the fold increase in MAFA expression versus untreated H1 human embryonic stem cells (Table 5), as measured by real-time PCR.

Treatment of cells expressing markers characteristic of the pancreatic endocrine lineage with compounds A4 (Cat #, 124001, Akt Inhibitor IV), E8 (Cat #527450, PKR Inhibitor), and F9 (Cat #539648, Staurosporine, N-benzoyl-) at a 2.5 µM concentration resulted in an increase in MAFA expression at least 4 fold higher than vehicle treated controls (Table 5). Treatment with the compound E6 (Cat #521233, PDGF Receptor Tyrosine Kinase Inhibitor IV) at a 2.5 µM concentration resulted in an increase in MAFA expression at least 2.5 fold higher than vehicle treated controls (Table 5).

Example 11

Screening of the Effects of Compounds from the EMD Kinase Inhibitor Library II on Cells Treated According to the Differentiation Protocol Outlined in Example 9

Cells of the human embryonic stem cell line H1 at passage 46 were seeded onto MATRIGEL®-coated 24-well dishes (1:30 dilution), and differentiated according to the methods described in Example 9 up to stage 5. Following this, the cells were fed and treated on day 1, 3, and 5 of stage 5 with media comprising DMEM-HG, 1% B27 (Invitrogen, CA), 1 µM ALK5 inhibitor II (Calbiochem, Ca) (Stage 5) and a compound from an EMD Calbiochem compound library II solubilized in DMSO (Tables 1 and 6, Calbiochem, San Diego, Calif.) and treated at a final concentration of 2.504. Wells containing vehicle were included as a control. Throughout the protocol media was changed daily except at stage 5 when media was changed every other day. All samples were treated in duplicate.

Figure 9:
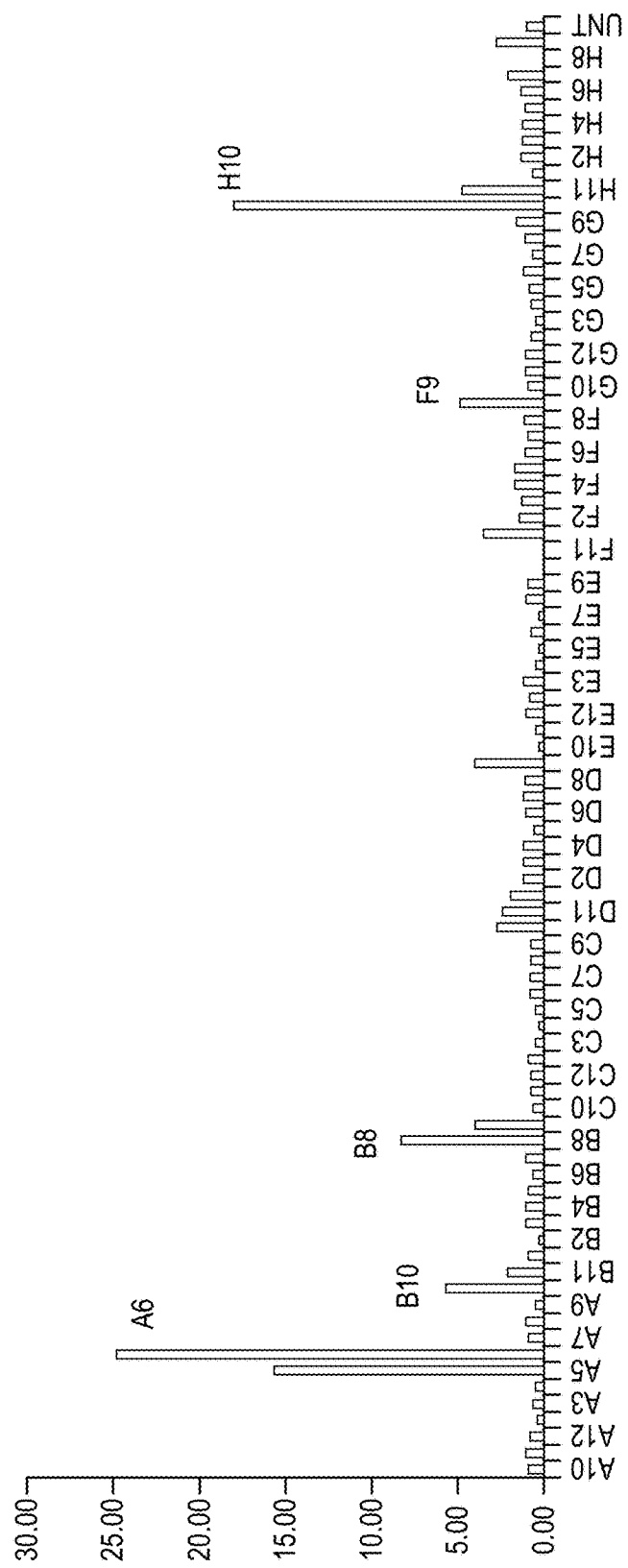
FIG. 9 shows the effect of compounds from the EMD Calbiochem kinase inhibitor library I on the expression of MAFA in cells expressing markers characteristic of the pancreatic endocrine lineage, as determined by real-time PCR.

At the completion of this treatment RNA was collected for PCR analysis. Samples were analyzed by real-time PCR for expression of MAFA. Results for compounds that stimulated the expression of MAFA are shown and expressed as the fold increase in MAFA expression versus control samples (FIG. 9), as measured by real-time PCR.

Treatment of cells expressing markers characteristic of the pancreatic endocrine lineage with either: Alsterpaullone, 2-Cyanoethyl; SU9516; Alsterpaullone; Cdk1/2 Inhibitor III; Casein Kinase I Inhibitor, D4476; or MEK1/2 Inhibitor at a 2.5 µM concentration resulted in a 4.5 fold increase in MAFA expression versus untreated controls (Table 7).

Example 12

Inhibiting Cell Cycle Progression in Cells Expressing Markers Characteristic of the Pancreatic Endocrine Lineage with Small Molecule Inhibitors Promotes MAFA Expression in Cells Expressing Markers Characteristic of the Pancreatic Endocrine Lineage Cell growth resulting from cell cycle progression can be activated and maintained by stimulating cells with extracellular growth factors. Growth factors bind to the extracellular domains of growth factor receptors, inducing a conformational switch in the receptor's intracellular domain. This shift initiates receptor dimerization and activation of tyrosine kinases located on the intracellular domain of the receptor leading to phosphorylation and activation of multiple serine/threonine kinases downstream, ultimately resulting in cell cycle progression and cell proliferation.

Under normal physiologic conditions mature pancreatic beta cells, characterized by expression of insulin and the transcription factor MAFA, are quiescent and tend to remain in G0 of the cell cycle. Yet, in order to generate enough cells to form a functional organ and meet the needs of a mature animal, the cells expressing markers characteristic of the pancreatic endocrine lineage of the present invention must be cell cycling. Consequently, at some point in embryonic development, the cells expressing markers characteristic of the pancreatic endocrine lineage of the present invention differentiate to beta cells and transition from an actively cell-cycling proliferating cell, to a quiescent cell.

Our data indicate that by inhibiting cell cycle progression by blocking signaling cascades with small molecule kinase inhibitors, we can induce the cells expressing markers characteristic of the pancreatic endocrine lineage to express MAFA, a marker of mature pancreatic beta cells. Kinase inhibitors targeted to a growth factor receptor, (PDGF Receptor Tyrosine Kinase Inhibitor IV), or inhibitors which disrupt kinases downstream of tyrosine kinase receptors (MEK1/2 Inhibitor, PKR Inhibitor, or Akt Inhibitor IV) disrupt proliferative growth factor/kinase based signaling resulting in cell cycle arrest and induction of MAFA expression. Use of a broad spectrum inhibitor like staurosporine, can effectively induce MAFA, however it is also cytotoxic at effective concentrations. More directed compounds like cyclin dependent kinase inhibitors (Alsterpaullone, 2-Cyanoethyl; SU9516; Alsterpaullone; or Cdk1/2 Inhibitor III) induce MAFA with less toxicity than a broad spectrum inhibitor like staurosporine.

In order to determine if a broad spectrum kinase inhibitor could induce MAFA expression and a more mature phenotype in the cells expressing markers characteristic of the pancreatic endocrine lineage of the present invention we differentiated H1 human ES cells according to the methods described in example 9, and treated them on days 1, 3, and 5 of stage 5 with the protein-tyrosine kinase inhibitor, Genistein, which has been shown to induce G2 phase arrest in human and murine cell lines and inhibit multiple kinases. At doses of 10 and 30 ng/ml the endocrine hormones insulin, somatostatin, and the transcription factor MAFA, all showed increased expression versus untreated controls, while at 10 ng/ml the endocrine hormone glucagon had increased expression (FIGS. 10A-D). We observed significant toxicity at a 100 ng/ml dose of genistein that correlated with loss of insulin, glucagon, and somatostatin expression.

These data indicate that by inhibiting cell cycle progression by blocking signaling cascades with small molecule kinase inhibitors targeted to inhibit signal transduction from a growth factor receptor tyrosine kinase through intracellular signaling kinases to the nucleus and cyclin dependent kinases, we can induce the cells expressing markers characteristic of the pancreatic endocrine lineage of the present invention to express MAFA, a marker of mature pancreatic beta cells.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

TABLE 1

AlphaNumeric Well Label and the Corresponding PubChem ID# for EMD Calbiochem ® Kinase Inhibitor II compound library

| Well | PubChemID# | Well | PubChemID# | Well | PubChemID# | Well | PubChemID# |
|---|---|---|---|---|---|---|---|
| A2 | 16760529 | B2 | 16760303 | C2 | 5330797 | D2 | 9797929 |
| A3 | 5278396 | B3 | 5326739 | C3 | 3004085 | D3 | 11493598 |
| A4 | 6605258 | B4 | 5353431 | C4 | 481747 | D4 | 16760417 |
| A5 | 5005498 | B5 | 2422 | C5 | 1893668 | D5 | 73292 |
| A6 | 16760286 | B6 | 5472558 | C6 | 9969021 | D6 | 4124851 |
| A7 | 5326843 | B7 | 2794188 | C7 | 2856 | D7 | 6539732 |
| A8 | 3641059 | B8 | 5330812 | C8 | 6918386 | D8 | 448014 |
| A9 | 6604931 | B9 | 438981 | C9 | 10202471 | D9 | 5287844 |
| A10 | 11524144 | B10 | 6419753 | C10 | 9549301 | D10 | 6538818 |
| A11 | 9549303 | B11 | 16760346 | C11 | 5339183 | D11 | 10020713 |
| E2 | 5312137 | F2 | 11382492 | G2 | 6419739 | H2 | 176155 |
| E3 | 6419766 | F3 | 11624601 | G3 | 4665 | H3 | 16219471 |
| E4 | 6419741 | F4 | 490561 | G4 | 4713 | H4 | 3387354 |
| E5 | 3674 | F5 | 3820 | G5 | 4712 | H5 | 5174 |
| E6 | 9903786 | F6 | 5312122 | G6 | 5164 | H6 | 5228 |
| E7 | 6419764 | F7 | 9951490 | G7 | 4987 | H7 | 16760659 |
| E8 | 8515 | F8 | 389898 | G8 | 9549289 | H8 | 451705 |
| E9 | 11665831 | F9 | 9549284 | G9 | 5702541 | H9 | 16760660 |
| E10 | 11422035 | F10 | 11644425 | G10 | 5162 | H10 | 5289419 |
| E11 | 16760525 | F11 | 509554 | G11 | 5353940 | H11 | 9549300 |

TABLE 2

The Effect of compounds of the BIOMOL Inhibitor compound library on the Ratio of Insulin/glucagon and MAFA/Arx4 expression as determined by real-time PCR in Cells Expressing Markers Characteristic of the Pancreatic Endocrine Lineage. The AlphaNumeric well# corresponds to the compound identity in Table 3.

| Well # | Ratio vs. Control Insulin to Glucagon | MAFA to Arx4 |
|---|---|---|
| B1 | 1.6 | 0.9 |
| B2 | 2.4 | 1.3 |
| B3 | 2.9 | 2.9 |
| B4 | 1.1 | 2.0 |
| B5 | 1.3 | 1.3 |
| B6 | 1.6 | 16.3 |
| B7 | 1.3 | 0.5 |
| B8 | 1.6 | 0.5 |
| B9 | 1.1 | 1.5 |
| B10 | 1.2 | 1.5 |
| B11 | 1.1 | 2.1 |
| B12 | 1.0 | 2.0 |
| C1 | 0.7 | 0.8 |
| C2 | 0.9 | 1.0 |
| C3 | 1.3 | 0.9 |
| C4 | 1.2 | 1.7 |
| C5 | 1.0 | 1.1 |
| C6 | 1.6 | 1.2 |
| C7 | 4.3 | 0.2 |
| C8 | 40.2 | 84.3 |
| C9 | 0.8 | 0.5 |
| C10 | 2.3 | 1.9 |
| C11 | 1.1 | 0.4 |
| C12 | 1.0 | 0.4 |
| D1 | 2.7 | 1.2 |
| D2 | 3.4 | 1.3 |
| D3 | 1.7 | 2.1 |
| D4 | 5.8 | 6.4 |
| D5 | 1.4 | 1.1 |
| D6 | 1.8 | 3.9 |
| D7 | 1.7 | 0.6 |
| D8 | 2.8 | 5.1 |
| D9 | 1842.5 | 212.6 |
| D10 | 0.9 | 1.3 |
| D11 | 1.0 | 0.7 |
| D12 | 1.1 | 2.5 |
| E1 | 1.1 | 0.9 |
| E2 | 0.8 | 0.8 |
| E3 | 1.2 | 1.0 |
| E4 | 2.1 | 1.3 |
| E5 | 1.3 | 1.1 |
| E6 | 2.0 | 1.5 |
| E7 | 4.8 | 0.2 |
| E8 | 3.7 | 0.0 |
| E9 | 1.0 | 0.8 |
| E10 | 0.6 | 0.2 |
| E11 | 1.0 | 0.3 |
| E12 | 0.8 | 0.2 |
| F1 | 10.3 | 9.5 |
| F2 | 2.9 | 1.9 |
| F3 | 2.6 | 2.5 |
| F4 | 1.5 | 2.7 |
| F5 | 1.9 | 1.4 |
| F6 | 1.6 | 1.2 |
| F7 | 1.9 | 0.6 |
| F8 | 1.5 | 0.6 |
| F9 | 1.0 | 1.4 |
| F10 | 5.4 | 3.4 |
| F11 | 0.8 | 1.9 |
| F12 | 1.0 | 1.4 |
| G1 | 0.8 | 1.2 |
| G2 | 0.6 | 1.1 |
| G3 | 2.0 | 1.6 |
| G4 | 1.3 | 1.6 |
| G5 | 1.7 | 1.5 |
| G6 | 1.5 | 1.3 |
| G7 | 4.6 | 0.2 |
| G8 | 3.9 | 0.4 |
| G9 | 1.0 | 0.7 |
| G10 | 1.3 | 0.7 |
| G11 | 1.9 | 0.6 |
| G12 | 1.4 | 0.8 |
| H1 | 3.1 | 0.6 |
| H2 | 1.8 | 3.5 |
| H3 | 1.8 | 3.9 |
| H4 | 1.2 | 4.0 |

TABLE 2-continued

The Effect of compounds of the BIOMOL Inhibitor compound library on the Ratio of Insulin/glucagon and MAFA/Arx4 expression as determined by real-time PCR in Cells Expressing Markers Characteristic of the Pancreatic Endocrine Lineage. The AlphaNumeric well# corresponds to the compound identity in Table 3.

| Well # | Ratio vs. Control Insulin to Glucagon | MAFA to Arx4 |
|---|---|---|
| H5 | 1.8 | 2.0 |
| H6 | 1.4 | 2.9 |
| H7 | 1.5 | 0.6 |
| H8 | 2.1 | 0.8 |
| vehicle control | 1.0 | 1.0 |

TABLE 3

AlphaNumeric Well Label and the Corresponding Catalog#, CAS#, and Compound Name or ID Number for the BIOMOL Kinase Inhibitor compound library

| PLATE LOCATION | CATALOG # | CAS # | COMPOUND NAME OR ID NUMBER |
|---|---|---|---|
| B1 | EI-360 | 167869-21-8 | PD-98059 |
| B2 | EI-282 | 109511-58-2 | U-0126 |
| B3 | EI-286 | 152121-47-6 | SB-203580 |
| B4 | EI-148 | 84477-87-2 | H-7 |
| B5 | EI-195 | 84468-17-7 | H-9 |
| B6 | EI-156 | 62996-74-1 | Staurosporine |
| B7 | EI-228 | 133550-35-5 | AG-494 |
| B8 | EI-267 | | AG-825 |
| B9 | EI-185 | 125697-92-9 | Lavendustin A |
| B10 | EI-253 | 136831-49-7 | RG-14620 |
| B11 | EI-191 | 118409-57-7 | Tyrphostin 23 |
| B12 | EI-187 | 118409-58-8 | Tyrphostin 25 |
| C1 | EI-257 | 122520-85-8 | Tyrphostin 46 |
| C2 | EI-188 | 122520-86-9 | Tyrphostin 47 |
| C3 | EI-189 | 122520-90-5 | Tyrphostin 51 |
| C4 | EI-190 | 2826-26-8 | Tyrphostin 1 |
| C5 | EI-335 | 116313-73-6 | Tyrphostin AG 1288 |
| C6 | EI-277 | 63177-57-1 | Tyrphostin AG 1478 |
| C7 | AC-1133 | 71897-07-9 | Tyrphostin AG 1295 |
| C8 | EI-215 | 10537-47-0 | Tyrphostin 9 |
| C9 | EI-247 | | HNMPA (Hydroxy-2-naphthalenylmethylphosphonic acid) |
| C10 | EI-370 | 120685-11-2 | PKC-412 |
| C11 | EI-271 | 10083-24-6 | Piceatannol |
| C12 | EI-275 | 172889-26-8 | PP1 |
| D1 | EI-272 | 133550-35-3 | AG-490 |
| D2 | EI-263 | | AG-126 |
| D3 | EI-229 | | AG-370 |
| D4 | EI-258 | | AG-879 |
| D5 | ST-420 | 154447-36-6 | LY 294002 |
| D6 | ST-415 | 19545-26-7 | Wortmannin |
| D7 | EI-246 | 133052-90-1 | GF 109203X |
| D8 | EI-226 | 548-04-9 | Hypericin |
| D9 | EI-283 | 138489-18-6 | Ro 31-8220 |
| D10 | EI-155 | 123-78-4 | Sphingosine |
| D11 | EI-196 | 127243-85-0 | H-89 |
| D12 | EI-158 | 84478-11-5 | H-8 |
| E1 | EI-184 | 91742-10-8 | HA-1004 |
| E2 | EI-233 | 103745-39-7 | HA-1077 |
| E3 | EI-232 | | HDBA (2-Hydroxy-5-(2,5-dihydroxybenzylamino)benzoic acid) |
| E4 | EI-230 | 127191-97-3 | KN-62 |
| E5 | EI-268 | | KN-93 |
| E6 | EI-197 | 109376-83-2 | ML-7 |
| E7 | EI-153 | 105637-50-1 | ML-9 |
| E8 | CC-100 | 452-06-2 | 2-Aminopurine |
| E9 | CC-202 | 158982-15-1 | N9-Isopropyl-olomoucine |
| E10 | CC-200 | 101622-51-9 | Olomoucine |
| E11 | CC-201 | 101622-50-8 | iso-Olomoucine |
| E12 | CC-205 | 186692-46-6 | Roscovitine |
| F1 | EI-293 | 24386-93-4 | 5-Iodotubercidin |
| F2 | EI-295 | 62004-35-7 | LFM-A13 |
| F3 | EI-294 | 152121-30-7 | SB-202190 |
| F4 | EI-297 | 172889-27-9 | PP2 |

TABLE 3-continued

AlphaNumeric Well Label and the Corresponding Catalog#, CAS#, and Compound Name or ID Number for the BIOMOL Kinase Inhibitor compound library

| PLATE LOCATION | CATALOG # | CAS # | COMPOUND NAME OR ID NUMBER |
|---|---|---|---|
| F5 | EI-298 | 208260-29-1 | ZM 336372 |
| F6 | EI-306 | 5812-07-7 | SU 4312 |
| F7 | EI-303 | 146535-11-7 | AG-1296 |
| F8 | EI-307 | 220904-83-6 | GW 5074 |
| F9 | AC-1121 | 6865-14-1 | Palmitoyl-DL-carnitine Cl |
| F10 | EI-270 | 82-08-6 | Rottlerin |
| F11 | EI-147 | 446-72-0 | Genistein |
| F12 | ST-110 | 486-66-8 | Daidzein |
| G1 | EI-146 | 63177-57-1 | Erbstatin analog |
| G2 | AC-1142 | 6151-25-3 | Quercetin dihydrate |
| G3 | AC-1293 | | SU1498 |
| G4 | EI-357 | 4452-06-6 | ZM 449829 |
| G5 | EI-278 | 195462-67-7 | BAY 11-7082 |
| G6 | EI-231 | 53-85-0 | DRB (5,6-Dichloro-1-(β-D-ribofuranosylbenzimidazole) |
| G7 | EI-273 | | HBDDE (2,2',3,3',4,4'-Hexahydroxy-1,1'-biphenyl-6,6'-dimethanol dimethyl ether) |
| G8 | EI-305 | 129-56-6 | SP 600125 |
| G9 | CC-206 | 479-41-4 | Indirubin |
| G10 | CC-207 | 160807-49-8 | Indirubin-3'-monoxime |
| G11 | EI-299 | 146986-50-7 | Y-27632 |
| G12 | EI-310 | 142273-20-9 | Kenpaullone |
| H1 | EI-328 | 121-40-4 | Terreic acid |
| H2 | EI-332 | 35943-35-2 | Triciribine |
| H3 | EI-336 | | BML-257 |
| H4 | EI-343 | | SC-514 |
| H5 | EI-344 | | BML-259 |
| H6 | EI-345 | 520-36-5 | Apigenin |
| H7 | EI-346 | | BML-265 (Erlotinib analog) |
| H8 | A-275 | 53123-88-9 | Rapamycin |

TABLE 4

The Effect of compounds of the BIOMOL Inhibitor compound library on the Expression of Insulin, glucagon, MAFA and Arx4 in Cells Expressing Markers Characteristic of the Pancreatic Endocrine Lineage

| Concentration and PubChem ID# | MAFA | Insulin | Glucagon | Arx4 |
|---|---|---|---|---|
| 0.61 μM 5330812 | 46.3 | 0.9 | 0.26 | 0.68 |
| 1.25 μM 5330812 | 209.2 | 1.3 | 0.31 | 0.66 |
| 5.0 μM 5330812 | 2909.9 | 66.3 | 4.71 | 0.92 |
| 0.61 μM 4566 | 1.0 | 1.0 | 0.77 | 0.78 |
| 1.25 μM 4566 | 0.8 | 1.1 | 0.90 | 0.78 |
| 5.0 μM 4566 | 1.0 | 1.1 | 0.96 | 0.69 |
| 0.61 μM 5330797 | 0.7 | 0.6 | 0.34 | 0.36 |
| 1.25 μM 5330797 | 1.5 | 0.8 | 0.25 | 0.37 |
| 5.0 μM 5330797 | 6.3 | 1.3 | 0.04 | 0.16 |
| 0.61 μM 73292 | 0.7 | 0.7 | 0.29 | 0.38 |
| 1.25 μM 73292 | 1.3 | 1.0 | 0.25 | 0.42 |
| 5.0 μM 73292 | 3.1 | 0.8 | 0.13 | 0.33 |
| 0.61 μM 4592 | 0.9 | 0.9 | 0.81 | 0.61 |
| 1.25 μM 4592 | 1.0 | 1.0 | 0.70 | 0.54 |
| 5.0 μM 4592 | 0.6 | 1.3 | 1.08 | 0.77 |
| 0.61 μM 160355 | 0.9 | 0.9 | 0.76 | 0.77 |
| 1.25 μM 160355 | 0.7 | 1.0 | 0.61 | 0.65 |
| 5.0 μM 160355 | 0.8 | 1.1 | 0.59 | 0.86 |
| Vehicle Treated | 1.0 | 1.0 | 1.00 | 1.00 |

TABLE 5

AlphaNumeric Well Label and the Corresponding Catalog#, and Compound Name or ID Number for the EMD Calbiochem Kinase Inhibitor compound library I

| Plate Location | Catalog# | Compound Name | Gene Induction vs. H1: MAFa |
|---|---|---|---|
| A10 | 197221 | Bcr-abl Inhibitor | 1.5 |
| A11 | 203290 | Bisindolylmaleimide I | 0.8 |
| A12 | DMSO | Control | 1.5 |
| A2 | 121767 | AG 1024 | 0.8 |
| A3 | 121790 | AGL 2043 | 0.8 |

TABLE 5-continued

AlphaNumeric Well Label and the Corresponding Catalog#, and Compound Name or ID Number for the EMD Calbiochem Kinase Inhibitor compound library I

| Plate Location | Catalog# | Compound Name | Gene Induction vs. H1: MAFa |
|---|---|---|---|
| A4 | 124011 | Akt Inhibitor IV | 45.7 |
| A5 | 124012 | Akt Inhibitor V, Triciribine | 0.9 |
| A6 | 124018 | Akt Inhibitor VIII, Isozyme-Selective, Akti-1/2 | 1.6 |
| A7 | 124020 | Akt Inhibitor X | 1.4 |
| A8 | 521275 | PDK1/Akt/Flt Dual Pathway Inhibitor | 2.1 |
| A9 | 189404 | Aurora Kinase Inhibitor II | 1.3 |
| B10 | 317200 | DMBI | 1.9 |
| B11 | 324673 | EGFR/ErbB-2 Inhibitor | 2.4 |
| B12 | DMSO | Control | 1.9 |
| B2 | 203297 | Bisindolylmaleimide IV | 1.9 |
| B3 | 203696 | BPIQ-I | 1.6 |
| B4 | 220285 | Chelerythrine Chloride | 2.3 |
| B5 | 234505 | Compound 56 | 1.8 |
| B6 | 260961 | DNA-PK Inhibitor II | 2.0 |
| B7 | 260962 | DNA-PK Inhibitor III | 2.2 |
| B8 | 528100 | PI-103 | 1.9 |
| B9 | 266788 | Diacylglycerol Kinase Inhibitor II | 1.5 |
| C10 | 375670 | Herbimycin A, *Streptomyces* sp. | 1.3 |
| C11 | 343022 | Flt-3 Inhibitor III | 1.1 |
| C12 | DMSO | Control | 1.1 |
| C2 | 324674 | EGFR Inhibitor | 3.5 |
| C3 | 324840 | EGFR/ErbB-2/ErbB-4 Inhibitor | 0.9 |
| C4 | 343020 | Flt-3 Inhibitor | 0.6 |
| C5 | 343021 | Flt-3 Inhibitor II | 0.5 |
| C6 | 344036 | cFMS Receptor Tyrosine Kinase Inhibitor | 2.2 |
| C7 | 365250 | Gö 6976 | 1.9 |
| C8 | 365251 | Gö 6983 | 1.0 |
| C9 | 371806 | GTP-14564 | 0.7 |
| D10 | 440203 | LY 303511 | 1.7 |
| D11 | 448101 | Met Kinase Inhibitor | 2.1 |
| D12 | BLANK | | 1.7 |
| D2 | 407248 | IGF-1R Inhibitor II | 1.6 |
| D3 | 407601 | IRAK-1/4 Inhibitor | 2.2 |
| D4 | 420099 | JAK Inhibitor I | 1.4 |
| D5 | 420104 | JAK3 Inhibitor II | 2.0 |
| D6 | 420121 | JAK3 Inhibitor IV | 1.7 |
| D7 | 420126 | JAK3 Inhibitor VI | 1.9 |
| D8 | 428205 | Lck Inhibitor | 1.9 |
| D9 | 440202 | LY 294002 | 2.3 |
| E10 | 528106 | PI 3-Kg Inhibitor | 1.6 |
| E11 | 528108 | PI 3-KbInhibitor II | 1.4 |
| E12 | BLANK | | 1.6 |
| E2 | 513035 | PD 158780 | 0.8 |
| E3 | 513040 | PD 174265 | 1.0 |
| E4 | 521231 | PDGF Receptor Tyrosine Kinase Inhibitor II | 0.8 |
| E5 | 521232 | PDGF Receptor Tyrosine Kinase Inhibitor III | 1.7 |
| E6 | 521233 | PDGF Receptor Tyrosine Kinase Inhibitor IV | 5.5 |
| E7 | 521234 | PDGF RTK Inhibitor | 1.9 |
| E8 | 527450 | PKR Inhibitor | 24.6 |
| E9 | 527455 | PKR Inhibitor, Negative Control | 1.5 |
| F10 | 567805 | Src Kinase Inhibitor I | 2.3 |
| F11 | 572660 | SU11652 | 1.7 |
| F12 | DMSO | Control | 2.1 |
| F2 | 529574 | PP3 | 1.3 |
| F3 | 529581 | PP1 Analog II, 1NM-PP1 | 2.3 |
| F4 | 539652 | PKCbII/EGFR Inhibitor | 1.8 |
| F5 | 539654 | PKCb Inhibitor | 1.6 |
| F6 | 553210 | Rapamycin | 1.2 |
| F7 | 555553 | Rho Kinase Inhibitor III, Rockout | 1.7 |
| F8 | 555554 | Rho Kinase Inhibitor IV | 2.3 |
| F9 | 539648 | Staurosporine, N-benzoyl- | 11.7 |
| G10 | 658550 | AG 1295 | 1.4 |
| G11 | 658551 | AG 1296 | 1.1 |
| G12 | DMSO | Control | 1.2 |
| G2 | 574711 | Syk Inhibitor | 1.2 |
| G3 | 574712 | Syk Inhibitor II | 0.8 |
| G4 | 574713 | Syk Inhibitor III | 1.1 |
| G5 | 616451 | TGF-b RI Kinase Inhibitor | 1.1 |
| G6 | 616453 | TGF-b RI Inhibitor III | 1.6 |
| G7 | 658390 | AG 9 | 1.5 |
| G8 | 658401 | AG 490 | 1.4 |

TABLE 5-continued

AlphaNumeric Well Label and the Corresponding Catalog#,
and Compound Name or ID Number for the EMD Calbiochem
Kinase Inhibitor compound library I

| Plate Location | Catalog# | Compound Name | Gene Induction vs. H1: MAFa |
|---|---|---|---|
| G9 | 658440 | AG 112 | 1.4 |
| H10 | 189405 | Aurora Kinase Inhibitor III | 2.0 |
| H11 | 569397 | Staurosporine, *Streptomyces* sp. | 0.0* |
| H12 | DMSO | Control | 1.5 |
| H2 | 658552 | AG 1478 | 2.7 |
| H3 | 676480 | VEGF Receptor 2 Kinase Inhibitor I | 1.7 |
| H4 | 676481 | VEGF Receptor Tyrosine Kinase Inhibitor II | 1.0 |
| H5 | 676482 | VEGF Receptor Tyrosine Kinase Inhibitor III, KRN633 | 1.6 |
| H6 | 676485 | VEGF Receptor 2 Kinase Inhibitor II | 1.0 |
| H7 | 676487 | VEGF Receptor 2 Kinase Inhibitor III | 1.1 |
| H8 | 676489 | VEGF Receptor 2 Kinase Inhibitor IV | 2.1 |
| H9 | 260964 | DNA-PK Inhibitor V | 1.5 |

TABLE 6

AlphaNumeric Well Label, Corresponding Catalog#,
and Compound # for EMD Calbiochem ®
Kinase Inhibitor II compound library

| Well # | Catalog # | Compound # |
|---|---|---|
| A1 | DMSO | |
| A2 | 422706 | KN-62 |
| A3 | 118500 | ATM Kinase Inhibitor |
| A4 | 118501 | ATM/ATR Kinase Inhibitor |
| A5 | 126870 | Alsterpaullone |
| A6 | 126871 | Alsterpaullone, 2-Cyanoethyl |
| A7 | 128125 | Aloisine A, RP107 |
| A8 | 128135 | Aloisine, RP106 |
| A9 | 164640 | Aminopurvalanol A |
| A10 | 171260 | AMPK Inhibitor, Compound C |
| A11 | 189405 | Aurora Kinase Inhibitor III |
| A12 | BLANK | |
| B1 | DMSO | |
| B2 | 189406 | Aurora Kinase/Cdk Inhibitor |
| B3 | 402085 | Indirubin-3'-monoxime |
| B4 | 196870 | BAY 11-7082 |
| B5 | 203600 | Bohemine |
| B6 | 217695 | Cdk1 Inhibitor |
| B7 | 217696 | Cdk1 Inhibitor, CGP74514A |
| B8 | 217714 | Cdk1/2 Inhibitor III |
| B9 | 217720 | Cdk1/5 Inhibitor |
| B10 | 218696 | Casein Kinase I Inhibitor, D4476 |
| B11 | 218710 | Casein Kinase II Inhibitor III, TBCA |
| B12 | BLANK | |
| C1 | DMSO | |
| C2 | 219476 | Cdk4 Inhibitor |
| C3 | 219477 | Cdk4 Inhibitor II, NSC 625987 |
| C4 | 219478 | Cdk4 Inhibitor III |
| C5 | 219479 | Cdc2-Like Kinase Inhibitor, TG003 |
| C6 | 220486 | Chk2 Inhibitor II |
| C7 | 234503 | Compound 52 |
| C8 | 238803 | Cdk2 Inhibitor III |
| C9 | 238804 | Cdk2 Inhibitor IV, NU6140 |
| C10 | 219491 | Cdk/Crk Inhibitor |
| C11 | 328009 | ERK Inhibitor III |
| C12 | BLANK | |
| D1 | DMSO | |
| D2 | 688000 | ROCK Inhibitor, Y-27632 |
| D3 | 328007 | ERK Inhibitor II, FR180204 |
| D4 | 328008 | ERK Inhibitor II, Negative control |
| D5 | 341251 | Fascaplysin, Synthetic |
| D6 | 361540 | GSK-3b Inhibitor I |
| D7 | 361541 | GSK-3b Inhibitor II |
| D8 | 361549 | GSK-3b Inhibitor VIII |
| D9 | 361550 | GSK-3 Inhibitor IX |
| D10 | 361551 | GSK-3 Inhibitor X |
| D11 | 361553 | GSK-3b Inhibitor XI |
| D12 | BLANK | |
| E1 | DMSO | |
| E2 | 572635 | SU6656 |
| E3 | 361555 | GSK-3 Inhibitor XIII |
| E4 | 371957 | Isogranulatimide |
| E5 | 400090 | IC261 |
| E6 | 401481 | IKK-2 Inhibitor IV |
| E7 | 402081 | Indirubin Derivative E804 |
| E8 | 420119 | JNK Inhibitor II |
| E9 | 420123 | JNK Inhibitor, Negative Control |
| E10 | 420129 | JNK Inhibitor V |
| E11 | 420136 | JNK Inhibitor IX |
| E12 | BLANK | |
| F1 | DMSO | |
| F2 | 475863 | MK2a Inhibitor |
| F3 | 420135 | JNK Inhibitor VIII |
| F4 | 420298 | K-252a, *Nocardiopsis* sp. |
| F5 | 422000 | Kenpaullone |
| F6 | 422708 | KN-93 |
| F7 | 444937 | MEK Inhibitor I |
| F8 | 444938 | MEK Inhibitor II |
| F9 | 444939 | MEK1/2 Inhibitor |
| F10 | 454861 | MNK1 Inhibitor |
| F11 | 481406 | NF-κB Activation Inhibitor |
| F12 | BLANK | |
| G1 | DMSO | |
| G2 | 506121 | p38 MAP Kinase Inhibitor III |
| G3 | 506126 | p38 MAP Kinase Inhibitor |
| G4 | 513000 | PD 98059 |
| G5 | 513030 | PD 169316 |
| G6 | 559396 | SB220025 |
| G7 | 540500 | Purvalanol A |
| G8 | 361554 | GSK3b Inhibitor XII, TWS119 |
| G9 | 371963 | H-89, Dihydrochloride |
| G10 | 559387 | SB 202474, Negative control for p38 MAPK inhibition studies |
| G11 | 559388 | SB 202190 |
| G12 | BLANK | |
| H1 | DMSO | |
| H2 | 559389 | SB 203580 |
| H3 | 371970 | HA 1077, Dihydrochloride Fasudil |
| H4 | 559402 | SB 218078 |
| H5 | 565625 | SC-68376 |
| H6 | 567305 | SKF-86002 |
| H7 | 567731 | Sphingosine Kinase Inhibitor |

TABLE 6-continued

AlphaNumeric Well Label, Corresponding Catalog#,
and Compound # for EMD Calbiochem ®
Kinase Inhibitor II compound library

| Well # | Catalog # | Compound # |
|---|---|---|
| H8 | 569397 | Staurosporine, *Streptomyces* sp. |
| H9 | 570250 | STO-609 |
| H10 | 572650 | SU9516 |
| H11 | 616373 | Tpl2 Kinase Inhibitor |
| H12 | BLANK | |

TABLE 7

Fold Induction of MAFA expression by several Compounds from the
EMD Kinase Inhibitor Library II on Cells Treated according to the
Differentiation Protocol Outlined in Example 9

| well# | fold vs. control | cat# | drug name |
|---|---|---|---|
| A6 | 24.8 | 126871 | Alsterpaullone, 2-Cyanoethyl |
| H10 | 18.0 | 572650 | SU9516 |
| A5 | 15.3 | 126870 | Alsterpaullone |
| B8 | 8.2 | 217714 | Cdk1/2 Inhibitor III |
| B10 | 5.7 | 218696 | Casein Kinase I Inhibitor, D4476 |
| F9 | 4.92 | 444939 | MEK1/2 Inhibitor |

What is claimed is:

1. A method for increasing the expression of insulin and MAF bZIP transcription factor A ("MAFA") in cells expressing markers characteristic of the pancreatic endocrine lineage comprising the steps of:
   a. sequentially differentiating human pluripotent stem cells to obtain cells expressing markers characteristic of the pancreatic endocrine lineage; and
   b. culturing the cells expressing markers characteristic of the pancreatic endocrine lineage in medium comprising an added amount of a cyclin-dependent kinase inhibitor to cause an increase in expression of insulin and MAFA as compared to cells expressing markers characteristic of the pancreatic endocrine lineage that are not cultured in medium comprising the added cyclin-dependent kinase inhibitor;
   wherein the cyclin-dependent kinase inhibitor is selected from group consisting of 5-amino-3-((4-(aminosulfonyl)phenyl)amino)-N-(2,6-difluorophenyl)-1h-1,2,4-triazole-1-carbothioamide and 2-bromo-12,13-dihydro-5H-indolo[2,3-a]pyrrolo[3,4-c]carbazole-5,7(6H)-dione.

2. The method of claim 1, wherein the cyclin-dependent kinase inhibitor is added to cells expressing markers characteristic of the endocrine lineage at a concentration from about 0.1 µM to about 10 µM for about one to seven days.

3. The method of claim 1, wherein the cells expressing markers characteristic of the pancreatic endocrine lineage are pancreatic endocrine cells.

4. The method of claim 1, wherein the cyclin-dependent kinase inhibitor is 5-amino-3-((4-(aminosulfonyl)phenyl)amino)-N-(2,6-difluorophenyl)-1h-1,2,4-triazole-1-carbothioamide.

5. The method of claim 1, wherein the cyclin-dependent kinase inhibitor is 2-bromo-12,13-dihydro-5H-indolo[2,3-a]pyrrolo[3,4-c]carbazole-5,7(6H)-dione.

6. A method for increasing the expression of insulin and MAF bZIP transcription factor A ("MAFA") in a population of cells comprising pancreatic endocrine cells comprising culturing the population of cells in medium comprising an added amount of a cyclin-dependent kinase inhibitor to cause an increase in the expression of insulin and MAFA in the population as compared to a population of cells comprising pancreatic endocrine cells not cultured in medium comprising the added cyclin-dependent kinase inhibitor, wherein the cyclin-dependent kinase inhibitor is selected from group consisting of 5-amino-3-((4-(aminosulfonyl)phenyl)amino)-N-(2,6-difluorophenyl)-1h-1,2,4-triazole-1-carbothioamide and 2-bromo-12,13-dihydro-5H-indolo[2,3-a]pyrrolo[3,4-c]carbazole-5,7(6H)-dione.

7. The method of claim 6, wherein the method comprises adding the cyclin-dependent kinase inhibitor at a concentration from about 0.1 µM to about 10 µM for about one to seven days.

8. The method of claim 6, wherein the cyclin-dependent kinase inhibitor is 5-amino-3-((4-(aminosulfonyl)phenyl)amino)-N-(2,6-difluorophenyl)-1h-1,2,4-triazole-1-carbothioamide.

9. The method of claim 6, wherein the cyclin-dependent kinase inhibitor is 2-bromo-12,13-dihydro-5H-indolo[2,3-a]pyrrolo[3,4-c]carbazole-5,7(6H)-dione.

10. The method of claim 6, wherein the pancreatic endocrine cells are obtained by differentiating human pluripotent stem cells.

11. The method of claim 10, wherein the human pluripotent stem cells are human embryonic cells.

* * * * *